(12) United States Patent
Lyon et al.

(10) Patent No.: US 7,595,191 B2
(45) Date of Patent: Sep. 29, 2009

(54) ISOLATION AND PURIFICATION OF P. FALCIPARUM MEROZOITE PROTEIN-142 VACCINE

(75) Inventors: Jeffrey A. Lyon, Silver Spring, MD (US); Evelina Angov, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 425 days.

(21) Appl. No.: 11/039,880

(22) Filed: Jan. 24, 2005

(65) Prior Publication Data

US 2006/0148010 A1    Jul. 6, 2006

Related U.S. Application Data

(62) Division of application No. 10/057,531, filed on Jan. 25, 2002, now Pat. No. 6,855,322.

(60) Provisional application No. 60/264,535, filed on Jan. 29, 2001.

(51) Int. Cl.
| | |
|---|---|
| C12N 15/00 | (2006.01) |
| C12P 21/06 | (2006.01) |
| C12N 15/09 | (2006.01) |
| C07H 21/02 | (2006.01) |
| C07H 21/04 | (2006.01) |
| A61K 39/015 | (2006.01) |

(52) U.S. Cl. .................. 435/320.1; 435/69.1; 435/69.3; 435/471; 536/23.1; 536/23.7; 424/268.1; 424/272.1

(58) Field of Classification Search ........................ None
See application file for complete search history.

(56) References Cited

U.S. PATENT DOCUMENTS 6,855,322 B2 *   2/2005   Lyon et al.   ............... 424/268.1

FOREIGN PATENT DOCUMENTS

WO    97/30159    8/1997

WO    00/63245    10/2000

OTHER PUBLICATIONS

Ausubel, pp. 10-58 to 10-62; A1-39.*
Pan et al., "Vaccine Candidate MSP-1 From *Plasmodium falciparum*: A Redesigned 4917 bp Polynucleotide Enables Synthesis And Isolation of Full-Length Protein From *Escherichia coli* And Mammalian Cells", Nucleic Acids Research, Oxford University Press, vol. 27(4):1094-1103, (1999).
Chang et al., "A Recombinant Baculovirus 42-Kilodalton C-Terminal Fragment of *Plasmodium falciparum* Merozoite Surface Protein 1 Protects Aotus Monkeys Against Malara", Infection and Immunity, American Society for Microbiology, vol. 64(1):253-261, (1996).
Kumar et al., "Immunogenicity and In Vivo Efficacy of Recombinant *Plasmodium falciparum* Merozoite Surface Protein-1 In Aotus Monkeys", Molecular Medicine, vol. 1(3):325-332, (1995).
Angov et al., "Process Development for Clinical Grade *Plasmodium falciparurn* MSP1/42 (3D7) Expressed in *E. coli*", XP008018167, p. 207, (1999).
Lalitha et al., "*Plasmodium falciparum*: Variations in the C-Terminal Cysteine-Rich Region of the Merozoite Surface Protein-1 In Field Samples Among Indian Isolates", Experimental Parasitology, Academic Press, vol. 92, pp. 12-18, (1999).
Dutta et al., "Purification, Characterization, and Immunogenicity Of A Disulfide Cross-Linked Plasmodium Vivax Vaccine Candidate Antigen, Merozoite Surface Protein 1, Expressed In *Escherichia coli*", Infection and Immunity, American Society for Microbiology, vol. 69(9):5464-5470, (2001).
Angov et al., "Development and Pre-Clinical Analysis of A *Plasmodium falciparum* Merozoite Surface Protein-$1_{42}$ Malaria Vaccine", Molecular & Biochemical Parasitology, vol. 128, pp. 195-204, (2003).
Kumar et al., 1995, Molecular Medicine 1, pp. 325-332.
Short Protocols in Molecular Biology Ed: Ausubel Publisher: John Wiley, pp. 10-59, 16-31, 16-32, 16-33 and 16-34.
Chang et al., 1996 Infection and Immunity 64: pp. 253-261.

* cited by examiner

*Primary Examiner*—Robert B Mondesi
*Assistant Examiner*—Padma V Baskar
(74) *Attorney, Agent, or Firm*—Elizabeth Arwine

(57) ABSTRACT

In this application is the expression and purification of a recombinant *Plasmodium falciparum* (3D7) MSP-$1_{42}$. The method of the present invention produces a highly purified protein which retains folding and disulfide bridging of the native molecule. The recombinant MSP-$1_{42}$ is useful as a diagnostic reagent, for use in antibody production, and as a vaccine.

9 Claims, 8 Drawing Sheets

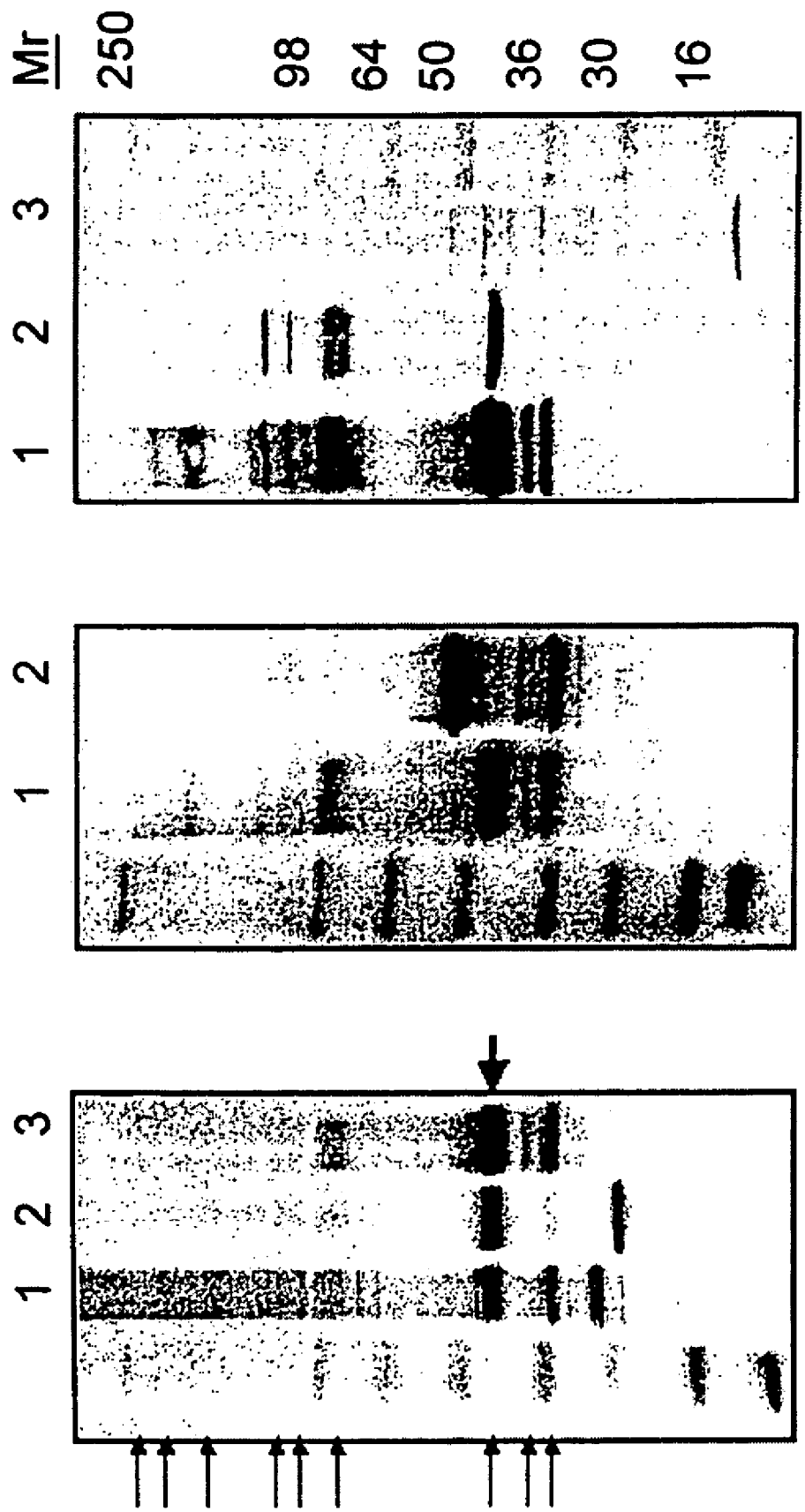

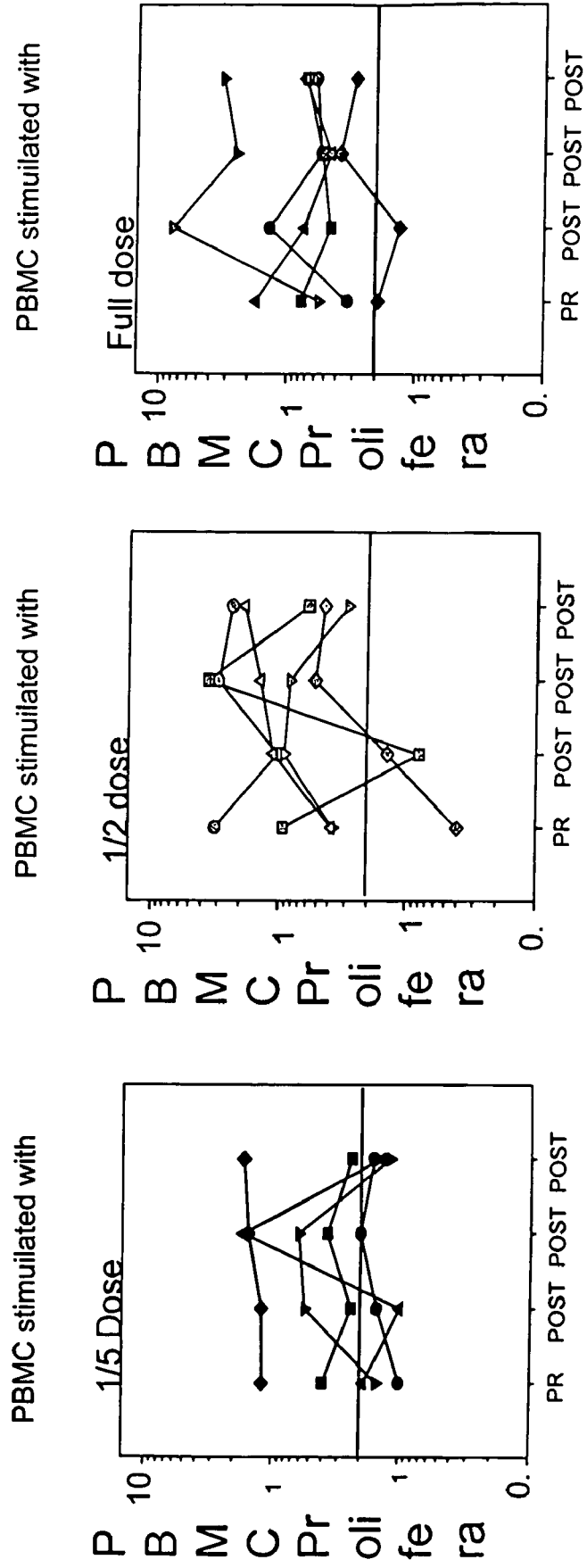

ISOLATION AND PURIFICATION OF *P. FALCIPARUM* MEROZOITE PROTEIN-142 VACCINE

This application claims the benefit of priority under 35 U.S.C. §119(e) from U.S. application Ser. No. 60/264,535 filed on Jan. 29, 2001, still pending and U.S. provisional application filed on Oct. 26, 2001, still pending. This application is a divisional of application Ser. No. 10/057,531, filed Jan. 25, 2002, issued as U.S. Pat. No. 6,855,322, which is incorporated herein by reference.

INTRODUCTION

*Plasmodium falciparum* is the leading cause of malaria morbidity and mortality. The World Health Organization estimates that approximately 200 million cases of malaria are reported yearly, with 3 million deaths (World Health Organization, 1997, Wkly. Epidemiol. Rec. 72:269-276). Although, in the past, efforts have been made to develop effective controls against the mosquito vector using aggressive applications of pesticides, these efforts ultimately led to the development of pesticide resistance. Similarly, efforts at treatment of the disease through anti-parasitic drugs led to parasite drug-resistance. As the anti-vector and anti-parasite approaches failed, efforts became focused on malaria vaccine development as an effective and inexpensive alternative approach.

However, the complex parasitic life cycle has further confounded the efforts to develop efficacious vaccines for malaria. The parasite's life cycle is divided between the mosquito-insect host and the human host. While in the human host, it passes through several developmental stages in different organellar environments, i.e. the liver stage, the red blood stage. Although conceptually simple, in reality the problems that must be considered when designing subunit vaccines for malaria are great. Antigen diversity is a characteristic that must be taken into account and includes a high degree of developmental stage specificity, antigenic variation and antigen polymorphism. Vaccine candidates have been identified from each of the parasite's developmental stages. The major merozoite surface protein-1, MSP-1, is among the leading erythrocytic stage vaccine candidates (Diggs, et al, 1993, Parasitol. Today 9: 300-302). The objective of erythrocytic stage vaccines is to diminish the level of parasitemia in the bloodstream and thus reduce the severity of disease.

Although the MSP-1 molecule has been studied extensively, its function is not fully understood. There is evidence that MSP-1 binds to erythrocytes and may have a role in erythrocyte invasion (Perkins and Rocco, 1988, J. Immunol. 141, 3190-3196; Holder, A. A., 1994, Parasitology 108 (Suppl.) S5-18).

MSP-1 is secreted as a membrane-anchored (Haldar et al., 1985, J. Biol. Chem. 260, 4969-4974) 195 kDa precursor that is proteolytically processed to products with nominal molecular masses of 83, 28-30, 38-45, and 42 kDa during merozoite development (Holder and Freem,an, 1984, Phils Trans R. Soc. Lond B. Bio. Sci. 307, 171-177; Lyon et al., 1987, J. Immunol, 138, 895-901; Holder et al., 1987, Parasitology 94, 199-208). These protein fragments form a non-covalent complex on the surface of merozoites (McBride and Heidrich, 1987, Parasitology 23, 71-84; Lyon, et al., 1987, supra) that remain attached to the merozoite surface through the C-terminal 42 kDa fragment (MSP-$1_{42}$). At the time of erythrocyte invasion MSP-$1_{42}$ is processed further to a 33 kDa fragment and a 19 kDa C-terminal fragment (MSP-$1_{19}$) (Blackman, et al., 1991, Mol. Biochem. Parasitol. 49, 35-44) which is bound to the merozoite surface through an N-glycosylphosphatidyl inositol anchor (GPI) (Haldar, et al., 1985, supra). This second proteolytic cleavage event results in the shedding of the non-covalent associated protein complex from the merozoite surface during invasion. During the invasion process, MSP-$1_{19}$ is present on ring forms in the newly invaded erythrocyte (Blackman, et al., 1990, J. Exp. Med. 172, 379-382). The apparent structure of MSP-$1_{19}$ is complex, containing 12 cysteines within a span of 100 amino acid residues, and is arranged as two tandem domains that are homologous with epidermal growth factor (EGF) (Blackman, et al., 1991, supra; Morgan et al., 2000, J. Biomol. NMR 17, 337-347). Each putative EGF-domain contains six cyteine residues that would form three disulfide bridges per domain, which force the assembly of several well defined discontinous epitopes (Farley and Long, 1995, Exp. Parasitol. 80, 328-332; McBride and Heidrich, 1987, supra; Uthaipibull et al, 2001, J. Mol. Biol. 307, 1381-1394).

Because age-dependent development of immunity to malaria is due, at least in part, to antibody against erythrocytic stage parasites (Cohen, S. et al., 1964, Nature 192, 733-737), a malaria vaccine should induce effective antibodies against this developmental stage. Evidence supporting the use of MSP-$1_{42}$ and MSP-$1_{19}$ in a malaria vaccine is extensive. MSP-$1_{19}$-specific mAbs inhibit *P. falciparum* growth in vitro (Blackman et al., 1990, supra) and passively protect mice against infection with *P. yoelii* (Majarian et al., 1984, J. Immunol. 132, 3131-3137; Ling et al., 1994, Parasite Immunol. 16, 63-67). Immunization of *Aotus* monkeys with native *P. falciparum* MSP-1 (Siddiqui, et al., 1987, Proc. Natl. Acad. Sci. USA 84, 3014-3018), or *S. cerevisiae* recombinant MSP-$1_{19}$ (Kumar et al., 1995, Mol. Med. 1, 325-332; Egan et al., 2000, Infect. Immun. 68, 1418-1427; Stowers et al. 2001, Trends Parasitol. 17, 415-419), protect against a homologous challenge. *E. coli*-expressed *P. yoelii* MSP-$1_{19}$ (Burns et al., 1989, J. Immunol. 143, 2670-2676) protects against a homologous challenge in rodent models. Antibodies raised against yeast MSP-$1_{19}$ grown in yeast weakly inhibit *Plasmodium* growth in vitro (Gozalo et al., 1998, Am. J. Trop. Med. Hyg. 59, 991-997) however this antigen lacks correct structure and induces a strong allergic response (Keitel, W. A., 1999, Vaccine 18, 531-539). MSP-$1_{19}$ may not be an optimal vaccine because it does not induce strong T-helper cell responses (Quin et al., 2001, Eur. J. Immunol. 31, 72-81). Poor MSP-$1_{19}$ T-cell immunogenicity may be a consequence of its structural stability, which allows it to resist proteolysis, and therefore to resist processing and presentation to the immune system.

Thus, MSP-$1_{42}$ may be a better choice as a vaccine candidate (Quin and Langhorne, 2001, Infect. Immun. 69, 2245-2251). Immunization of *Aotus* monkeys with baculovirus-expressed recombinant MSP-$1_{42}$, protects against a homologous challenge and the anti-sera raised, inhibit *P. falciparum* growth in vitro, but do not result in sufficient yield and are not yet available in clinical grade ((Chang et al., 1996, Infect. Immun. 64, 253-261; Chang et al., 1992, J. Immunol. 149, 548-555). Monoclonal antibodies that either protect against infection in vivo (Burns et al., 1989, J. Immunol. 143, 2670-2676), or inhibit parasite growth in vitro (Blackman et al., 1990, supra), are specific for discontinuous epitopes since they do not react with disulfide-reduced MSP-$1_{19}$ (McBride and Heidrich, 1987, supra; Farley and Long, 1995, Exp. Parasitol. 80, 328-332). Thus, a recombinant vaccine produced from this part of the MSP-1 will require correct disulfide-dependent conformation to elicit a protective antibody response.

Therefore, heterologous expression of recombinant molecules must replicate the conformation and structure of these proteins to induce an appropriate immune response. Heterologous expression of recombinant (MSP-$1_{42}$) from eukaryotic expression systems, i.e. baculovirus and yeast, have lead to recombinant molecules that possess post-translational modifications due to N-glycosylation, and are expressed poorly or are misfolded. Post-translational modification due to N-glycosylation may be problematic for malaria vaccines because malaria parasites lack this ability.

Other attempts at producing MSP-1 in *E. coli* have not produced protective vaccines (Kumar, S. et al., 1995, Molecular Medicine 1, 325-332) due to problems with endotoxin contamination and possibly to an inability to establish correct disulfide bridging patterns.

Previous attempts show that not only is a good expression system needed for proper and sufficient expression of MSP-$1_{42}$ but, in addition, a good purification protocol is required which removes endotoxin contamination but which retains the proper folding of the antigen for presentation to the immune system.

SUMMARY OF THE INVENTION

The present invention satisfies the needs discussed above. The present invention provides a method for proper expression and purification of the MSP-$1_{42}$ 3D7 allele. The method of the present invention results in elimination of contaminating proteins and conservation of the native folding and disulfide bridging of the protein. Therefore, the essentially purified MSP-$1_{42}$ protein of the present invention retains proper conformation for optimal reactivity for vaccine and screening purposes.

Therefore, a major aim of the present invention resides in the production of large amounts of MSP-$1_{42}$ which maintain conformational epitopes critical to epitope formation in pure form (>95% pure) for diagnostic, prophylactic and therapeutic purposes.

This may not seem complicated but, as with most strategies for protein purification, proved to be difficult and unpredictable. *E. coli* was chosen as a host, even though it had gone out of favor, for two reasons: (1) *E. coli* was known to produce high level of recombinant proteins and (2) recombinant proteins produced in *E. coli* are not glycosylated, which is consistent with the capabilities of malaria parasites. Several hurdles had to be overcome to achieve the desired expression level in soluble cytoplasmic form which can be sufficiently purified from host cell proteins without sacrificing proper folding of the protein. Problems with *E. coli* endotoxin levels, antibiotic resistance and the presence of non-MSP-$1_{42}$ contaminants had to be resolved.

The final expression construct, pETATPfMSP-1.sub.42 (3D7) (deposited with ATCC under the Budapest Treaty on May 18, 2004, accession number PTA-5976), was the product of a series of subclonings, with each successive construction reducing the amount of expressed non-MSP-1 sequence. The construction of a DNA vector expressing a *P. falciparum* 3D7 MSP-$1_{42}$ molecule proceeded through several steps. A full-length fusion with *E. coli* thioredoxin at the N-terminus of MSP-$1_{42}$ was prepared by cloning in the multiple cloning region of the pET32a expression vector (Construct #1, FIG. 1A, pET-Trx42). The expressed protein is identified in SEQ ID NO:1. Positive clones were transformed into the highly regulatable T7 RNA polymerase expressing host. Mini-induction experiments were conducted to optimize expression levels of several clones. In these experiments some variables that were investigated included induction temperature, concentration of inducer (IPTG), length of time of induction, and the influence of *E. coli* host background on levels of expression [BL21 (DE3) versus AD494 (DE3)]. These variables have been shown to affect the levels of expression and the partitioning of protein in either soluble or insoluble fractions. SDS-PAGE and immunoblotting analysis of crude extracts from cells induced at 37° C. showed that the full length fusion, trxA-MSP-1.sub.42 (Construct #1, FIG. 1A) comprised greater than 20% of the total *E. coli* protein. However, following cell lysis, all of the fusion protein partitioned into the insoluble fraction and was associated with inclusion bodies. This situation is often the case with heterologous proteins that are expressed at high levels in *E. coli*.

with *E. coli* thioredoxin at the N-terminus of MSP–$1_{42}$ was prepared by cloning in the multiple cloning region of the pET32a expression vector (Construct #1, FIG. 1A, pET-Trx42). The expressed protein is identified in SEQ ID NO:1. Positive clones were transformed into the highly regulatable T7 RNA polymerase expressing host. Mini-induction experiments were conducted to optimize expression levels of several clones. In these experiments some variables that were investigated included induction temperature, concentration of inducer (IPTG), length of time of induction, and the influence of *E. coli* host background on levels of expression [BL21 (DE3) versus AD494 (DE3) ]. These variables have been shown to affect the levels of expression and the partitioning of protein in either soluble or insoluble fractions. SDS-PAGE and immunoblotting analysis of crude extracts from cells induced at 37° C. showed that the full length fusion, trxA-MSP-$1_{42}$ (Construct #1, FIG. 1A) comprised greater than 20% of the total *E. coli* protein. However, following cell lysis, all of the fusion proten partitioned into the insoluble fraction and was associated with inclusion bodies. This situation is often the case with heterologous proteins that are expressed at high levels in *E. coli*.

Lowering the culture temperature sequentially from 37° C. to 25° C. during induction of expression resulted in increasing levels of soluble fusion protein in the post-sonication supernatant. By increasing the soluble protein at this stage, a urea solubilization and refolding step is avoided thereby assuring more native folding of the protein. The post sonication soluble supernatant was applied to a $Ni^{+2}$=NTA agarose affinity column (QIAGEN) and bound protein was eluted with stepwise increasing gradients of imidazole. The expressed thioredoxin-MSP-$1_{42}$ fusion products from these cells was reactive with mAb 5.2 (see Table 1) on immunoblots. Our data suggested that this expression system would provide sufficient levels of recombinant protein for development as a diagnostic and vaccine antigen, providing proper covalent disulfide bridging could be achieved. A second construct was designed (Construct #2, pET(50)MSP-$1_{42}$) to delete the *E. coli* trxA gene (thioredoxin protein) from Construct #1 (thioredoxin-MSP-$1_{42}$ fusion). This product was developed as an alternative to the full-length thioredoxin fusion to address potential FDA regulatory concerns with a thioredoxin-MSP-$1_{42}$ fusion protein vaccine. The product formed retains the His6-tag for affinity purification and an additional vector encoded sequence (approximately 50 amino acids) which include an enterokinase cleavage site, and S-peptide tag, and the thrombin cleavage site fused to the N-terminus of MSP-$1_{42}$. The expressed product is identified in SEQ ID NO:2. The levels of expression from this construct were estimated at approximately 5-10% of the total *E. coli* protein from crude cell lysates and protein was purified to near homogeneity (>85%) with two consecutive passes over a $Ni^{+2}$-NTA agarose resin.

TABLE 1

MSP-1<sub>19</sub>-Specific Monoclonal Antibodies

| Antibody | Immunizing parasite | Stages | Epitope/location | Ref. |
|---|---|---|---|---|
| 2.2-7 | Thai-K1 | smr* | Conserved/EGF-like domain 1 | McKay |
| 12.8-2-1 | Thai-T9-96 (K1 like) | smr | Conserved/EGF-like domain 1 | Conway |
| 7.5-1 | Thai-K1 | smr | Semi-conserved/EGF-like domain 1 | McBride |
| 12.10-5-1 | Thai-T9-96 (K1 like) | smr | Semi-conserved, EGF-like domain 1&2 | Blackman |
| 5.2 | Uganda-Palo Alto (3D7 like) | smr | Semi-conserved, EGF-like domain 1 | Chang |
| 7F1 | Malayan Camp (3D7 like) | sm | MSP-133Strain Specific | Lyon |
| Polyclonal | 3D7 MSP-1-42 | smr | Many epitopes | Angov |

*-schizonts, merozoites, rings
References:
Blackman, M. J., et. al. 1990, J. Exp. Med. 172: 379-382.
Conway, D. J., et al. 1991, Parasitol. 103: 1-6.
Chang, S. P. et. al. 1988, Exp. Parasitol. 67: 1-11.
Mackay, M, et. al. 1985, EMBO J. 4: 3823-3829.
McBride, J. S., et. al. 1982, Science, 217: 254-257.
Lyon, J. A. et al. 1987, J. Immunology. 138: 895-901.
Polyclonal rabbit MSP-142 antibody was prepared at Walter Reed Army Institute of Research Department of Immunology, by immunization of rabbits with recombinant E. coli-expressed MSP-142 (3D7) adjuvanted with Complete Freunds Adjuvant.

Since the levels of expression and apparent protein folding of Construct #2 suggested that a correctly folded non-thioredoxin-fused MSP-1$_{42}$ was expressible, a third construct was developed to remove the entire vector non-MSP-1 encoded sequence fused at the N-terminus of Construct #2. This upstream gene sequence was deleted and was replaced with an annealed oligonucleotide linker to regenerate the His6-tag (Construct #3, pET42A). Therefore, Construct #3 contains 9 non-MSP-1$_{42}$ amino acids that include the His6 and 3 linker amino acids. The expressed product is identified in SEQ ID NO:3. The non-fused MSP-1$_{42}$ molecule from this construct is produced to adequate levels (2-5%) of the total E. coli protein and is correctly folded based on immunoreactivity with a series of MSP-1$_{19}$ specific mAbs (See Table 1). Potential regulatory concerns over selection in the presence of ampicillin resulted in a final modification on the His6-MSP-1$_{42}$ construct (Construct #3) that included the gene for tetracycline (Construct #4, pET-IEGR-MSP142(AT), FIG. 1B). Therefore, the plasmid designated as Construct #4 (also His6-MSP-1$_{42}$, but selectable with tetracycline) can be selected in the presence of tetracycline alone during large-scale fermentation or with ampicillin, as necessary. The expressed protein of Construct #4 is identified in SEQ ID NO:3. The final plasmid pET(AT)PfMSP-1$_{42}$(3D7) was created by removing the residual Factor Xa cleavage site. Constructs 1-4 can be used to produce fusion proteins with MSP-1$_{42}$ as a source of soluble antigen.

Intensive investigation of variables that affect the efficiency of fermentation and induction of expression were required to optimize His6-MSP-1$_{42}$ expression. Some variables which have a significant effect on target protein yields and bear upon purification strategies include the effects of media composition, amount of inducer necessary, temperature at which inducer is added to the cultures, and length of time of induction, to name a few.

A low temperature of induction was necessary in order to obtain soluble protein. The temperature of the cultures had to be reduced from 37° C. to about 25° C. prior to induction. At all higher temperatures, protein was found in inclusion bodies and difficult to isolate. Similarly, we found that the time of induction was important for proper and maximal expression of the protein. The length of IPTG induction was most advantageous at 2-3 hours. Induction for less time resulted in suboptimal protein synthesis and induction for more time resulted in loss of product due to lysis and protein degradation.

Cells were suspended in lysis buffer and lysed by microfluidization (Microfluidics) in one pass while the temperature of the sample was maintained below 10° C. at all times to reduce proteolysis. The lysate was centrifuged and the pellets and supernates were evaluated by immunoblotting.

The clarified lysate was then purified by several methods. The first method is using the ability of the His6-tag sequence expressed as a short N-terminal fusion on the target protein to bind to divalent cations, i.e. nickel, immobilized onto matrices. The w/v cell paste to resin ratio were varied to optimize yield and purity of the product and to minimize cost.

After elution of the protein from the Ni$^{2+}$ chelate resin, it is allowed to incubate at 0-4° C. overnight to promote disulfide bridge formation. This step is required because protein disulfide bridge formation does not occur readily in the cytoplasm of the E. coli BL21 DE3 expression host due to the reducing nature of this environment. This explains our observation that monoclonal antibodies known to react with properly folded disulfide bridged MSP-1$_{42}$ do not react with this protein either in cell lysates, or with partially purified recombinant MSP-1$_{42}$ immediately after its elution from the Ni$^{+2}$ NTA affinity column. Incubating the eluted protein at 0-4° C. for up to 48 hours following the Ni$^{+2}$ chromatography promotes proper disulfide bridge formation because after this incubation, all of the monoclonal antibodies now react with the antigen. These data suggest that at the time of lysis and chromatography on the Ni$^{+2}$ NTA affinity column the protein is probably folded properly through ionic and hydrophobic interactions, but that the disulfide bridges do not form until the protein is maintained in an oxidative environment over the observed period of time.

The eluted sample was then applied to a Q ion exchange chromatography column. Binding of the sample to the column was checked at varying pH values ranging from pH 6.2 to 9.9. In order to define a pH condition at which the protein would bind to the Q resin, we varied buffer types, e.g. phosphate (pH 6-9) vs. glycine (pH 8.5-11) vs. citrate (pH 4-5-6). Under the final conditions selected, MSP-1$_{42}$ partitioned into the flow through and most residual host cell remained proteins bound to the column.

Finally, CM ion exchange chromatography was used to remove low levels of residual E. coli protein and endotoxin. Variables optimized included the binding of protein to the column, the salt concentration of the washing and eluting solution.

The purified P. falciparum MSP-1$_{42}$ was used as a vaccine along with an adjuvant, for example, ADJUVANT B, and was found to elicit malaria specific antibody responses in monkeys. More importantly, vaccination with the MSP-1$_{42}$ elicited neutralizing antibodies and protects monkeys against a malaria infection.

Therefore, it is an object of the present invention to provide a recombinant P. falciparum MSP-1$_{42}$ for use in diagnostic assays and for production of antibodies.

It is another object of the present invention to provide compositions comprising purified recombinant P. falciparum MSP-1$_{42}$.

It is yet another object of the present invention to provide novel vector constructs for recombinantly expressing *P. falciparum* MSP-1$_{42}$, as well as host cells transformed with said vector.

It is also an object of the present invention to provide a method for producing and purifying recombinant *P. falciparum* MSP-1$_{42}$ protein comprising:

growing a host cell containing a vector expressing *P. falciparum* MSP-1$_{42}$ proteins in a suitable culture medium, causing expression of said vector sequence as defined above under suitable conditions for production of soluble protein and, lysing said transformed host cells and recovering said MSP-1$_{42}$ protein such that it retains its native folding and is essentially free of host toxins.

It is also an object of the present invention to provide diagnostic and immunogenic uses of the recombinant *P. falciparum* MSP-1$_{42}$ protein of the present invention, as well as to provide kits for diagnostic use for example in malaria screening and confirmatory antibody tests.

It is also an object of the present invention to provide monoclonal or polyclonal antibodies, more particularly human monoclonal antibodies or mouse monoclonal antibodies which are humanized, which react specifically with MSP-1$_{42}$ epitopes, either comprised in peptides or conformational epitopes comprised in recombinant proteins.

It is also an object of the present invention to provide possible uses of anti-MSP-1$_{42}$ monoclonal antibodies for malaria antigen detection or for therapy of chronic malaria infection.

It is yet another object of the present invention to provide a malaria vaccine comprising MSP-1$_{42}$ of the present invention, in an amount effective to elicit an immune response in an animal against *P. falciparum*; and a pharmaceutically acceptable diluent, carrier, or excipient.

It is another object of the present invention to provide a method for eliciting in a subject an immune response against malaria, the method comprising administering to a subject a composition comprising MSP-1$_{42}$ of the present invention. In one aspect of the invention, the DNA vaccine is delivered along with an adjuvant, for example ADJUVANT B.

It is another object of the present invention to provide a method for preventing malaria infection in an animal comprising administering to the animal the MSP-1$_{42}$ of the present invention.

The vaccine according to the present invention is inherently safe, is not painful to administer, and should not result in adverse side effects to the vaccinated individual.

The present invention also provides vectors for the production of a recombinant MSP-1$_{42}$, host cells containing the vectors, a method for fermenting and inducing the host cells, and a method for isolating and purifying the recombinant protein. Also provided is a method for bulk fermentation and expression of MSP-1$_{42}$.

All the objects of the present invention are considered to have been met by the embodiments as set out below.

BRIEF DESCRIPTION OF THE DRAWINGS

FIGS. 2A, 2B and 2C: SDS-PAGE analysis of MSP-1$_{42}$ during Purification and of the Final Product (FMP1). Protein detected by Coomassie Blue staining (2A and 2B) and immunoblotting (2C). 2A, non-reduced samples: lane 1, nickel chelate eluate; lane 2, Q flow through; lane 3 CM eluate. 2B, 10 ug FMP1 electrophoresed under non-reduced (lane 1) or reduced (lane 2) conditions. 2C, immunoblotting of 1 ug of FMP electrophoresed under non-reducing: lane 1 mAb 7F1; lane 2, mAb 12.10; lane 3, rabbit anti-*E. coli* antiserum.

FIGS. 6A-6F: CMI responses to FMP1/ADJUVANT B. Peripheral blood mononuclear cells (PBMC) were stimulated with FMP1 (top) or *P. falciparum* parasitized erythrocytes (PBRC, bottom) and proliferation was measured by 3H-thymidine uptake. Each panel contains data from all individuals within a vaccine group and individuals are differentiated by symbol. Samples were collected prior to immunization (pre) and two weeks following each immunization (post 1, post 2, post 3).

DETAILED DESCRIPTION

Figure 1A:
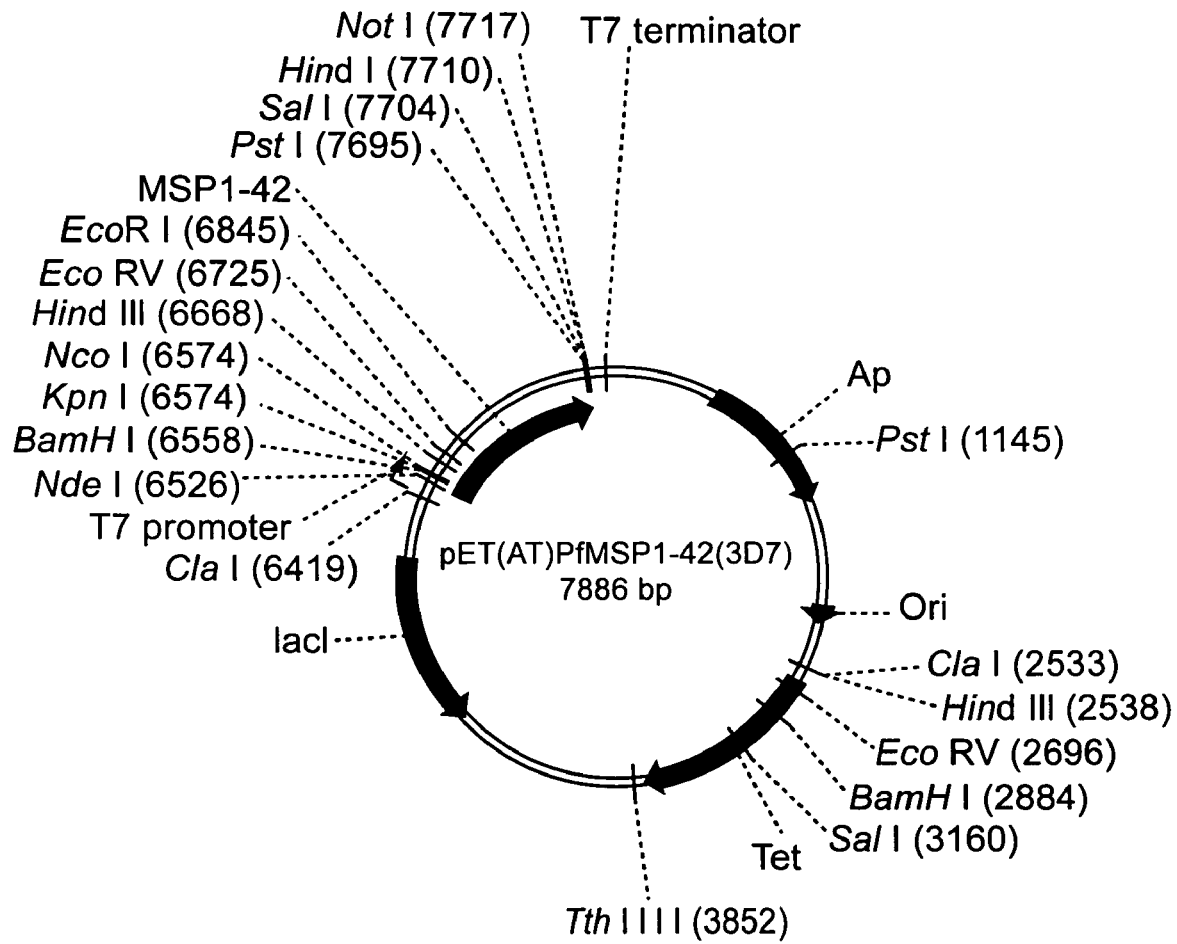
FIG. 1A: pET32a plasmid map.

In the description that follows, a number of terms used in recombinant DNA, parasitology and immunology are extensively utilized. In order to provide a clearer and consistent understanding of the specification and claims, including the scope to be given such terms, the following definitions are provided.

In general, an 'epitope' is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to *Plasmodium* such as 3D7, FVO and CAMP, or any other known or newly defined *Plasmodium* strain.

The term 'solid phase' intends a solid body to which the individual *P. falciparum* antigen is bound covalently or by noncovalent means such as hydrophobic, ionic, or van der Waals association.

The term 'biological sample' intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. falciparum* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism. Some biological fluids are used as a source of other products, such as clotting factors (e.g. Factor VIII; C), serum albumin, growth hormone and the like.

The term 'immunologically reactive' means that the antigen in question will react specifically with anti-MSP-1 antibodies present in a body component from a malaria infected individual.

The term 'immune complex' intends the combination formed when an antibody binds to an epitope on an antigen.

The term 'MSP-$1_{42}$' as used herein refers to the polymorphic C-terminal 42 kDa protein fragment or polypeptide resulting from the processing by proteases of the 195 kDa membrane-anchored MSP-1 precursor. During merozoite invasion, the 42 kDa fragment is subjected to secondary processing producing a 33-kDa fragment (MSP-$1_{33}$) and a 19 kDa C-terminal fragment, (MSP-$1_{19}$) which remains attached via GPI to the surface of the invading merozoite. The MSP-$1_{42}$ protein extends from approximately amino acid (aa) 1327 to about aa 1700 of the full-length precursor protein (Genbank accession #Z35327).

The term 'MSP-$1_{42}$' as used herein also includes analogs and truncated forms that are immunologically cross-reactive with natural MSP-$1_{42}$. By 'MSP-$1_{42}$' is intented MSP-$1_{42}$ from other strains of *Plasmodium*, or any other newly identified strain of *Plasmodium*.

The term 'homo-oligomer' as used herein refers to a complex of MSP-$1_{42}$ containing more than one MSP-$1_{42}$ monomer, e.g. MSP-$1_{42}$/MSP-$1_{42}$ dimers, trimers or tetramers, or any higher-order homo-oligomers of MSP-$1_{42}$ are all 'homo-oligomers' within the scope of this definition. The oligomers may contain one, two, or several different monomers of MSP-$1_{42}$ obtained from different strains of *Plasmodium falciparum* including for example 3D7, Camp, FVO, and others. Such mixed oligomers are still homo-oligomers within the scope of this invention, and may allow more universal diagnosis, prophylaxis or treatment of malaria.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' MSP-$1_{42}$ protein intends a *Plasmodium* protein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term 'therapeutic' refers to a composition capable of treating malaria infection.

The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of MSP-1$_{42}$ for prophylaxis of malaria disease are about 0.01 to 1000 ug/dose, more preferably about 0.1 to 100 ug/dose, most preferably about 10-50 ug/dose. Several doses may be needed per individual in order to achieve a sufficient immune response and subsequent protection against malaria.

More particularly, the present invention contemplates essentially purified MSP-1$_{42}$ and a method for isolating or purifying recombinant MSP-1$_{42}$ protein, characterized in that upon lysing the transformed host cells to isolate the recombinantly expressed protein, the disulfide bonds necessary for proper folding of the protein are preserved.

The term 'MSP-1$_{42}$' refers to a polypeptide or an analogue thereof (e.g. mimotopes) comprising an amino acid sequence (and/or amino acid analogues) defining at least one MSP-1$_{42}$ epitope. Typically, the sequences defining the epitope correspond to the amino acid sequence of MSP-1$_{42}$ region of *P. falciparum* (either identically or via substitution of analogues of the native amino acid residue that do not destroy the epitope). The MSP-1$_{42}$ protein corresponds to a nucleotide sequence identified in SEQ ID NO:5 and spans from amino acid 1327 to 1701 of MSP-1 3D7 allele (SEQ ID NO:6). Upon expression in the parasite system (non-glycosylated), it is believed to have an approximate molecular weight of 42 kDa as determined by SDS-PAGE. It is understood that these protein endpoints are approximations (e.g. the carboxy terminal end of MSP-1$_{42}$ could lie somewhere in the 1700 to 1720 amino acid region). The absolute C-terminus is not defined due to the post-translational modification that transfers MSP-1 to a GPI lipid membrane anchor.

The MSP-1$_{42}$ antigen used in the present invention is preferably a full-length protein, or a substantially full-length version, i.e. containing functional fragments thereof (e.g. fragments which are not missing sequence essential to the formation or retention of an epitope). Furthermore, the *P. falciparum* antigen of the present invention can also include other sequences that do not block or prevent the formation of the conformational epitope of interest. The presence or absence of a conformational epitope can be readily determined though screening the antigen of interest with an antibody as described in the Examples below (polyclonal serum or monoclonal to the conformational epitope) and comparing its reactivity to that of a denatured version of the antigen which retains only linear epitopes (if any).

The *P. falciparum* antigen of the present invention can be made by any recombinant method that provides the epitope of interest. For example, recombinant expression in *E. coli* is a preferred method to provide non-glycosylated antigens in 'native' conformation. This is most desirable because natural *P. falciparum* antigens are not glycosylated. Proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts such as baculovirus and yeast or higher eukaryotes, as long as glycosylation is inhibited.

The proteins according to the present invention may be secreted or expressed within compartments of the cell. Preferably, however, the proteins of the present invention are expressed within the cell and are released upon lysing the cells.

It is also understood that the isolates used in the examples section of the present invention were not intended to limit the scope of the invention and that an equivalent sequence from a *P. falciparum* isolate from another allele, e.g. FVO, or CAMP, can be used to produce a recombinant MSP-$1_{42}$ protein using the methods described in the present application. Other new strains of *Plasmodium* may be a suitable source of MSP-$1_{42}$ sequence for the practice of the present invention.

The MSP-$1_{42}$ protein of the present invention is expressed as part of a recombinant vector. The present invention relates more particularly to the MSP-$1_{42}$ nucleic acid sequence in recombinant nucleic acids pETATpfMSP-$1_{42}$(3D7) as represented in SEQ ID NO:7 or parts thereof. The MSP-$1_{42}$ genomic sequence was cloned into pET32a from Novagen (Madison, Wis.). This plasmid comprises, in sequence, a T7 promoter, optionally a lac operator, a ribosome binding site, restriction sites to allow insertion of the structural gene and a T7 terminator sequence. Other vectors provided include pET-Trx42, pET(50)MSP-$1_{42}$m pET42A, pET-IEGR-MSP-$1_{42}$ (AT) all described below in Materials and Methods. Examples of other plasmids which contain the T7 inducible promoter include the expression plasmids pET-17b, pET-11a, pET-24a-d(+), and pEt-9a, all from Novagen (Madison, Wis.); see the Novagen catalogue.

The present invention also contemplates host cells transformed with a recombinant vector as defined above. In a preferred embodiment, *E. coli* strain BL21 (DE3) (F-ompT hsdSB(rB-mB-) gal dcm (DE3)) is employed. The above plasmids may be transformed into this strain or other strains of *E. coli* having the following characteristics: a T7 RNA polymerase rec gene, Lon, ompT protease mutants or any other *E. coli* with a protease deficiency such as *E. coli* origami. Preferably, the host includes BL21(DE3) and any of its precursors. Other host cells such as insect cells can be used taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, including HeLa cells, Chinese hamster ovary (CHO) cells, Baby hamster kidney (BHK) cells, PK15, RK13 and a number of other cell lines. MSP-$1_{42}$ expressed in these cells will be glycosylated unless the cells have been altered such that glycosylation of the recombinant protein is not possible. It is expected that when producing MSP-$1_{42}$ in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. Host cells provided by this invention include *E. coli* containing pET-Trx42, *E. coli* containing pET(50)MSP-$1_{42}$, and *E. coli* containing pET42A, *E. coli* containing pET-IEGR-MSP-$1_{42}$(AT), and *E. coli* containing pET(AT) PfMSP-$1_{42}$(3D7).

A preferred method for isolating or purifying MSP-$1_{42}$ as defined above is further characterized as comprising at least the following steps:

(i) growing a host cell as defined above transformed with a recombinant vector expressing MSP-$1_{42}$ proteins in a suitable culture medium, (ii) causing expression of said vector sequence as defined above under suitable conditions for production of a soluble protein, (iii) lysing said transformed host cells and recovering said MSP-$1_{42}$ protein such that it retains its native conformation and is essentially pure.

Once the host has been transformed with the vector, the transformed cells are grown in culture in the presence of the desired antibiotic. For FDA regulatory purposes, it is preferable to use tetracycline or kanamycin. When cells reach optimal biomass density, in this case about 0.4 OD 600 in small culture flasks or 4-6 OD 600 in bulk fermentors, the cells are induced to produce the recombinant protein. The inventors have found after trial and error that for expression of a soluble MSP-$1_{42}$, it was necessary to cool the culture to a range of about 10° C.-20° C., more preferably about 15° C.-28° C., most preferably about 24 to 26° C. prior to induction. The concentration of inducer, i.e. IPTG, added affects the maximal protein synthesis. It was found that a concentration of 0.1 mM IPTG was best, however, a range of 0.05 to 0.5 mM would be sufficient to produce 80-100% of maximal.

The cells were then collected and lysed to release the recombinant protein. Preferably, lysis should occur at a paste to buffer ratio of 1:3 w/v to reduce viscosity and volume of sample loaded on Ni-NTA column. Preferably, lysis is in the presence of imidazole which reduces non specific binding of *E. coli* protein to Ni resin, and benzonase which is able to digest *E. coli* nucleic acids at a reduced temperature. Lysis is preferably at a temperature of about 0° C.-24° C., more preferably about 5-15° C. in order to retain native folding of the MSP-$1_{42}$ protein and to reduce proteolysis. A high salt concentration of about 0.5-1.0 M is preferable. Salts used include NaCl or other monovalent ions.

Preferably, the *E. coli* endotoxin is separated and removed from the recombinant protein. This can be done several ways. For MSP-$1_{42}$, endotoxin was removed by applying to a $Ni^{+2}$-NTA column. The removal of endotoxin depended on washing at low pH, about 5.8 to 6.5, preferably about pH 6.2, in high salt, about 0.5 to about 1.0 mM, preferably about 500 mM NaCl at a flow rate of about 20 to about 35 ml/min, preferably about 30 ml/min. The cell paste to resin ratio can be about 5:1 to about 7:1 w/v, preferably about 6:1 w/v. The recombinant protein can be eluted by addition of high pH buffer of about 7.5 to about 8.5, preferably about pH 8.0, in a phosphate buffer of about 10-20 mM, more preferably about 10 mM sodium phosphate buffer.

At this point the recombinant protein is about 50% pure. If further purity is required, ion-exchange chromatography can be utilized. The column is preferably with an ionic character such that a pH to reduce protein binding and promote endotoxin and nucleic acid binding can be used.

Finally, the flow through sample (about 0.1 mg/ml), can be subjected to further ion exchange chromatography for further concentration and purification. The MSP-$1_{42}$ of the present invention was subjected to CM ion exchange chromatography. The pH of the buffer can be about 5.2 to about 6.2, preferably about 6.0. The salt concentration is about 25 mM to about 50 mM, preferably about 35 mM.

The bulk process for the isolation of purified MSP-1$_{42}$ differs little from the process described above. The concentration of imidazole is changed to about 120 mM to about 200 mM, preferably about 160 mM in order to specifically elute MSP-1$_{42}$.

The present invention further relates to a composition comprising at least one of the following MSP-1$_{42}$ peptides as listed in Table 3:

MSP-1$_{42}$ alone (SEQ ID NO:5) spanning amino acids to 1326-1701 of MSP-1,

MSP-1$_{42}$ with thioredoxin from vector pET-Trx 42 (SEQ ID NO:1);

MSP-1$_{42}$ without thioredoxin from vector pET(5)MSP-1$_{42}$ (SEQ ID NO:2);

MSP-1$_{42}$ plus His6tag produced from vector pET42A (SEQ ID NO:3)

MSP-1$_{42}$ without Factor Xa from vector pET-IEGR-MSP-1$_{42}$ (AT) (SEQ ID NO:3);

MSP-1$_{42}$ plus 17 amino acids at N-terminal in final construct (SEQ ID NO:3), from construct pET(AT)PfMSP-1$_{42}$ (3D7), the final expressed product referred to as FMP-1 (SEQ ID NO:7).

The present invention also relates to a composition comprising peptides or polypeptides as described above, for in vitro detection of malaria antibodies present in a biological sample.

The present invention also relates to a composition comprising at least one of the following MSP-1$_{42}$ conformational epitopes:

epitope recognized by monoclonal antibodies 12.10, 12.8, 7.5, 2.2, 1E1 (Blackman et al., 1990, supra; Conway et al., 1991, Parasitology 103, 1-6; McBride et al., 1982, Science 217, 254-257; Mackay et al., 1985, Embo J. 4, 3823-3829).

epitope recognized by monoclonal antibody 5.2 (Chang et al., 1988, Exp. Parasitol. 67, 1-11), and epitope recognized by monoclonal antibody 7F1 (Lyon et al., 1987, J. Immunol. 138, 895-901).

The present invention also relates to an MSP-1$_{42}$ specific antibody raised upon immunizing an animal with a peptide or protein composition, with said antibody being specifically reactive with any of the polypeptides or peptides as defined above, and with said antibody being preferably a monoclonal antibody.

The present invention also relates to an MSP-1$_{42}$ specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The MSP-1$_{42}$ specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from a certain strain may be used as a medicament, more particularly for incorporation into an immunoassay for the detection of *Plasmodium* strains for detecting the presence of MSP-1$_{42}$ antigens, or antigens containing MSP-1$_{42}$ epitopes, for prognosing/monitoring of malaria disease, or as therapeutic agents.

Alternatively, the present invention also relates to the use of any of the above-specified MSP-1$_{42}$ monoclonal antibodies for the preparation of an immunoassay kit for detecting the presence of MSP-1$_{42}$ antigen or antigens containing MSP-1$_{42}$ epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least the following steps:

(i) contacting said biological sample with any of the MSP-1$_{42}$ specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of MSP-1$_{42}$ antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to MSP-1$_{42}$, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-MSP-1$_{42}$ response (Linthicum, D. S. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., NH$_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

The present invention more particularly relates to a composition comprising at least one of the above-specified peptides or a recombinant MSP-1$_{42}$ protein composition as defined above, for use as a vaccine for immunizing a mammal, preferably humans, against malaria, comprising administering a sufficient amount of the composition possibly accompanied by pharmaceutically acceptable adjuvant(s), to produce an immune response.

Immunogenic compositions can be prepared according to methods known in the art. The present compositions comprise an immunogenic amount of a recombinant MSP-1$_{42}$ proteins or peptides as defined above, usually combined with a pharmaceutically acceptable carrier, preferably further comprising an adjuvant.

The proteins of the present invention, preferably purified MSP-1$_{42}$ derived from pETATPfMBP-1$_{42}$ (3D7) or FMP-1, are expected to provide a particularly useful vaccine antigen, since the antigen is able to induce invasion inhibitory antibodies as well as high titer antibodies that react with schizont-infected erythrocytes.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine(nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

Adjuvants used in the examples below include:

Adjuvant A, described in WO 96/33739, with the formulation 0.25 mg cholesterol, 1 mg dioleoyl phosphotidylcholine, 50 ug 3D-MPL, and 50 ug QS21 and consisting of small liposomes wherein the QS21 and the 3D-MPL are in the membranes of the liposomes;

Adjuvant B, described in U.S. Pat. No. 6,146,632, with the formulation 10.68 mg squalene, 11.86 mg tocopherol, 4.85 mg Tween 80, 50 ug 3D-MPL, and 50 ug QS21 and consisting of an oil-in water emulsion comprising the squalene and alpha-tocopherol, the emulsion being in admixture with the QS21 and 3-DPML;

Adjuvant C, described in WO 96/33739, with the formulation 0.25 mg cholesterol, 1 mg dioleoyl phosphotidylcholine, 50 ug 3D-MPL, 50 ug QS21 and 0.5 mg $AlOH_3$ and consisting of small liposomes wherein the saponin (QS21) and the LPS-derivative (3D-MPL) are in the membranes of the liposomes and wherein the liposomes and the antigen are absorbed onto a metallic salt particle carrier ($AlOH_3$);

Adjuvant D, with the formulation 0.5 mg $AlOH_3$, 500 ug of unmethylated immunostimulatory oligonucleotide CpG described in WO 96/02555 (CpG=5'-tcg tcg ttt tgt cgt ttt gtc gtt) (SEQ ID NO:8) where antigen and immunostimulant (CpG) are absorbed onto a metallic salt particle carrier ($AlOH_3$);

Adjuvant E, described in WO 96/33739, with the formulation 0.25 mg cholesterol, 1 mg dioleoyl phosphotidylcholine, 50 ug QS21, and 0.5 mg $AlOH_3$, consisting of small unilamellar vesicles wherein the saponin (QS21) is in the membranes of the vesicles and wherein the vesicles and the antigen are absorbed onto a metallic salt particle $AlOH_3$.

All documents cited herein are hereby incorporated by reference thereto.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The $MSP-1_{42}$ proteins of the invention may also be incorporated into Immune Stimulating Complexes together with saponins, for example QuilA (IS-COMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present homologous (e.g. other malaria antigens, such as EBA-175 or AMA-1) or heterologous (non-malaria) antigens. In this use, the proteins of the invention provide an immunogenic carrier capable of stimulating an immune response to other antigens. The antigen may be conjugated either by conventional chemical methods, or may be cloned into the gene encoding $MSP-1_{42}$ fused to the 5'end or the 3' end of the $MSP-1_{42}$ gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compounds, whether antibodies or vaccines, disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The present invention also relates to a method for in vitro diagnosis of malaria antibodies present in a biological sample, comprising at least the following steps (i) contacting said biological sample with a composition comprising any of the MSP-1$_{42}$ peptides as defined above, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from *Plasmodium* or other types of malaria parasite, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, possibly also including an automated scanning and interpretation device for inferring the malaria parasite present in the sample from the observed binding pattern.

The immunoassay methods according to the present invention utilize MSP-1$_{42}$ domains that maintain linear (in case of peptides) and conformational epitopes (proteins) recognized by antibodies in the sera from individuals infected with a malaria parasite. The MSP-1$_{42}$ antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™1 or Immunlon™2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The MSP-1$_{42}$ proteins, peptides, or antigens of the present invention will typically be packaged in the form of a kit for use in these immunoassays. The kit will normally contain in separate containers the MSP-1$_{42}$ antigen, control antibody formulations (positive and/or negative), labeled antibody when the assay format requires the same and signal generating reagents (e.g. enzyme substrate) if the label does not generate a signal directly. The MSP-1$_{42}$ antigen may be already bound to a solid matrix or separate with reagents for binding it to the matrix. Instructions (e.g. written, tape, CD-ROM, etc.) for carrying out the assay usually will be included in the kit.

Immunoassays that utilize the MSP-1$_{42}$ antigen are useful in screening blood for the preparation of a supply from which potentially infective malaria parasite is lacking. The method for the preparation of the blood supply comprises the following steps. Reacting a body component, preferably blood or a blood component, from the individual donating blood with MSP-1$_{42}$ proteins of the present invention to allow an immunological reaction between malaria antibodies, if any, and the MSP-1$_{42}$ antigen. Detecting whether anti-malaria antibody—MSP-1$_{42}$ antigen complexes are formed as a result of the reacting. Blood contributed to the blood supply is from donors that do not exhibit antibodies to the native MSP-1 antigens.

The present invention further contemplates the use of MSP-1$_{42}$ proteins, or parts thereof as defined above, for in vitro monitoring malaria infection or prognosing the response to treatment (for instance with chloroquine, mefloquine, Malarome) of patients suffering from malaria infection comprising:

incubating a biological sample from a patient with malaria infection with an MSP-1$_{42}$ protein or a suitable part thereof under conditions allowing the formation of an immunological complex, removing unbound components, calculating the anti-MSP-1$_{42}$ titers present in said sample (for example at the start of and/or during the course of therapy), monitoring the natural course of malaria infection, or prognosing the response to treatment of said patient on the basis of the amount anti-MSP-1$_{42}$ titers found in said sample at the start of treatment and/or during the course of treatment.

Patients who show a decrease of 2, 3, 4, 5, 7, 10, 15, or preferably more than 20 times of the initial anti-MSP-1$_{42}$ titers could be concluded to be long-term, sustained responders to malaria therapy.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one MSP-1$_{42}$ peptide as defined above, a buffer or components necessary for producing the buffer enabling the binding reaction between these proteins or peptides and the anti-MSP-1$_{42}$ antibodies present in a biological sample, means for detecting the immune complexes formed in the preceding binding reaction, possibly also an automated scanning and interpretation device for inferring a decrease of anti-MSP-1$_{42}$ titers during the progression of treatment.

The present invention also relates to a serotyping assay for detecting one or more serological types or alleles of malaria parasite present in a biological sample, more particularly for detecting antibodies of the different types or alleles of malaria parasites to be detected combined in one assay format, comprising at least the following steps:

(i) contacting the biological sample to be analyzed for the presence of malaria antibodies of one or more serological types, with at least one of the MSP-1$_{42}$ compositions as defined above, preferentially in an immobilized form under appropriate conditions which allow the formation of an immune complex, (ii) removing unbound components, (iii) incubating the immune complexes formed with heterologous antibodies, with said heterologous antibodies being conjugated to a detectable label under appropriate conditions, (iv) detecting the presence of said immune complexes visually or mechanically (e.g. by means of densitometry, fluorimetry, calorimetry) and inferring the presence of one or more malaria serological types present from the observed binding pattern.

It is to be understood that the compositions of proteins or peptides used in this method are recombinantly expressed type-specific or allele-specific proteins or type-specific peptides.

The present invention further relates to a kit for serotyping one or more serological types or alleles of malaria parasite present in a biological sample, more particularly for detecting the antibodies to these serological types of malaria parasites comprising:

at least one MSP-1$_{42}$ protein or MSP-1$_{42}$ peptide, as defined above, a buffer or components necessary for producing the buffer enabling the binding reaction between these proteins or peptides and the anti-MSP-1 antibodies present in a biological sample, means for detecting the immune complexes formed in the preceding binding reaction, possibly also an automated scanning and interpretation device for detecting the presence of one or more serological types present from the observed binding pattern.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Construction of Expression Cassette pET(AT)PfMSP-1$_{42}$ (3D7)

Molecular cloning and bacterial transformations were performed as described (Sambrook et al., Molecular cloning: A Laboratory Manual, Cold Spring Harbor Laboratory Press, 1989). The final expression construct, pETATPfMSP-142 (3D7) Tolle et al., 1995, Exp. Parasitol. 81, 47-54, was the product of a series of subclonings, each successive construction reducing the amount of expressed non-MSP-1 sequence. The MSP-1$_{42}$ fragment was prepared by PCR of genomic DNA using the forward primer GGGGATCCATTGAGGGTCGTGGTACCATGGCAATATCTGTCACAATGG (SEQ ID NO:9) and the reverse primer GTCGACTTAGGAACTGCAGAAAATACCGG (SEQ ID NO:10). The product was cloned into the expression vector pMAL-p (New England Biolabs) via the 5' BamHI and the 3' SalI site, sequenced (SEQ ID NO:4), and then subcloned into pET32a (Novagen, Madison, Wis.), creating pET-Trx42, which contained the MSP-1$_{42}$ gene fragment fused in-frame to the 3' end of the *E. coli* thioredoxin gene, trx. pET-Trx42 was digested with NdeI and religated to remove trx, creating pET(50)MSP-1$_{42}$. pET42A was created by digesting both the pET(50)MSP-1$_{42}$ vector and the DNA fragment GGGCATATGGCACACCATCATCATCATCATCCCGGGGGATCCGAC (SEQ ID NO: 11) with NdeI and BamHI and then ligating the two. The DNA fragment encoded six consecutive histidine residues and a short flexible linker sequence. To avoid using ampicillin selection, tet was subcloned from pBR322 by digesting with EcoRI and PflMI, then blunt-ending and ligating it into the Bst1107 I site in pET42A creating pET-IEGR-MSP-1$_{42}$ (AT). The final plasmid pET(AT)PfMSP-1$_{42}$(3D7) was created by removing the residual Factor Xa cleavage site. This was accomplished by digesting pET-IEGR-MSP-1$_{42}$(AT) and the DNA fragment GGGCATATGGCACACCATCATCATCATCATCCCGGGGGATCCGGTTCTGGTACCGAC (SEQ ID NO:12), with NdeI and KpnI and then ligating. 3D7 MSP-1$_{42}$ was expressed from this final construct with 17 non-MSP-1$_{42}$ amino acids fused to the N-terminus.

Expression of MSP-1$_{42}$.

The expression host, BL21 DE3 (F-ompT hsdSB(rB-mB-) gal dcm (DE3)) was transformed with pETATPfMSP-1$_{42}$ (3D7). Fresh stationary phase cultures of transformed bacteria were used to inoculate 1 L shake flasks of Super Broth containing 15 ug/ml tetracycline, which were grown to 0.4 OD 600 at 37° C. cooled to temperatures ranging from 25-35° C. and induced with 0.1 mM IPTG. Cell pastes were collected in lysis buffer (10 mM NaPO$_4$, pH 6.2, 50 mM NaCl, 10 mM imidazole, 2 mM MgCl$_2$, 50 U/ml benzonase) at a paste to buffer ratio of 1:3 w/v. Cells were lysed by microfluidization (Microfluidics) in one pass, NaCl was added to a final concentration of 500 mM. The temperature of the sample was maintained below 10° C. at all times. Tween-80, 1.0% w/v (final concentration), was added and the lysate was centrifuged at 27,666×g for 1 hr at 4° C. Pellets and supernates were evaluated by immunoblotting.

Bulk Fermentation and Expression of MSP-1$_{42}$ (3D7).

A 300 L fermentor of Super Broth supplemented with 15 ug/ml tetracycline was inoculated with three L of fresh stationary phase culture in accordance with Batch Production Record (BPR)-305-00. Fermentation continued until an OD 600=4.0-6.0 was reached. The fermentor was cooled to 25° C. prior to induction with 0.1 mM IPTG. Three hours following induction, cells were harvested by centrifugation at 15,000 rpm at 3 L/min. The cell paste was stored at −80° C. in the WRAIR Department of Biologics Research, Pilot Bioproduction Facility.

GMP Purification of *E. coli* Expressed MSP-1$_{42}$ (3D7), BPR-335-02. Cell paste was lysed as described above. Tween-80 was added to 1% w/v (final), and the lysate was centrifuged at 27,666×g for 1 hr at 4° C. The clarified lysate was collected and placed on ice. All further steps were carried out at 4° C.

Ni$^{+2}$ NTA Superflow (Qiagen, Germany): A column with a 6:1 w/v cell paste to resin ratio, was equilibrated with 10 mM NaPO$_4$, pH 6.2, 500 mM NaCl, 10 mM imidazole (Ni-buffer) supplemented with 0.5% Tween 80 (w/v). The clarified lysate was applied at a flow rate of 30 ml/min and the column washed with 1.1 volumes of Ni-buffer containing 0.5% Tween-80. The column was then washed with 30 volumes of Ni-buffer containing 0.5% Tween 80 (w/v); 20 volumes of 10 mM NaPO$_4$, pH 6.2, 75 mM NaCl, 10 mM imidazole; and 15 volumes of 10 mM NaPO$_4$, pH 8.0, 75 mM NaCl, 20 mM imidazole. MSP-1$_{42}$ was eluted with 10 volumes 10 mM NaPO$_4$, pH 8.0, 75 mM NaCl, 160 mM imidazole, and was diluted with an equal volume of 10 mM NaPO$_4$, 75 mM NaCl, pH 8.0, and 0.4% Tween 80.

Q ion exchange chromatography: A Toyopearl SuperQ 650 M (TosoHaas) column (cell paste: resin ratio=3:1 w/v), was equilibrated with 10 mM NaPO$_4$, pH 8.0, 75 mM NaCl, 80 mM imidazole, 0.2% Tween 80 (Q-buffer). The diluted sample was applied at a flow rate of 30 ml/min and washed with one volume of Q-buffer, which was combined with the flow through to pool the MSP-1$_{42}$, giving a final volume of this pool equal to 50 Q column volumes. This sample was diluted with an equal volume of 10 mM NaPO$_4$, pH 6.0, 0.4% Tween 80 (v/v), and the pH of the sample was adjusted to pH 6.0 with 6N HCl.

CM ion exchange chromatography: A CM 650 M (Toso-Haas) column (cell paste:resin ratio=2:1) was equilibrated with 10 mM NaPO$_4$, pH 6.0, 35 mM NaCl, 0.2% Tween 80 (CM-equilibration buffer) and the sample was applied at a flow rate of 30 ml/min. The column was washed with 6 volumes of CM-equilibration buffer, followed by 10 volumes of 10 mM NaPO$_4$, pH 7.0, 100 mM NaCl, 0.02% Tween 80 (v/v). The MSP-1$_{42}$ was eluted with 10 mM NaPO$_4$, pH 7.2, 250 mM NaCl in three column volumes.

SDS-PAGE and Immunoblotting. Protein samples were separated under reducing (10% 2-mercaptoethanol) or non-reducing conditions by SDS-PAGE with Tris-Glycine buffering (Invitrogen). Protein was detected by Coomassie Blue R250 staining. Immunoblotting was performed with nitrocellulose membranes (Invitrogen) blocked using 5% nonfat dry milk and 0.1% Tween 20 in PBS, pH 7.4. Blots were probed with polyclonal rabbit anti-MSP-1$_{42}$ antibodies or mAbs diluted into phosphate buffered saline, pH 7.4 containing 0.1% Tween 20. This buffer was also used for washing. The second antibodies were alkaline phosphatase-conjugated anti-rabbit IgG or anti-mouse IgG (H+L) (Promega, Madison, Wis.) and reactions were detected with nitro-blue tetrazolium and 5-bromo-4-chloro-3-indolyl phosphate (Sigma Chemicals, St. Louis, Mo.) in 100 mM NaCl, 5 mM MgCl$_2$, 100 mM Tris-HCl, pH 9.5. mAbs used for evaluation of structure included 2.2 (Mackay et al., 1985, Embo J. 4, 3823-3829), 12.8 (Conway et al, 1991, Parasitology 103, 1-6), 7.5 (McBride et al., 1982, Science 217, 254-257), 12.10 (Blackman et al., 1990, supra), 5.2 (Chang et al., 1988, Exp. Parasitol. 67, 1-11), and 7F1 (Lyon et al., 1987, J. Immunol. 138, 895-901).

Antigen Stability Studies

Stability studies were conducted for 18 months on MSP-1$_{42}$ stored at 40° C., −20° C., and −80° C. and for lyophilized product stored at −20° C. Stability was evaluated by Commassie Blue staining and immunoblotting of SDS PAGE gels run under non-reduced and reduced conditions.

Vaccine Preparation

The CM eluate was concentrated two-fold to 0.5 mg/ml, the buffer was exchanged with 10 volumes of phosphate buffered saline by diafiltration and the protein was sterilized by filtration through a Millipak 60 0.22-um filtration unit. Final bulk antigen (FMP1) was stored at −80° C. To prepare the antigen for use with adjuvant ADJUVANT B (GlaxoSmithKline Biologicals, Rixensart, Belgium), 118.5 ml of sterile purified FMP1 was mixed with 236 ml of 50 mM Na Phosphate, 101 ml of 15.75% lactose, and 0.5 ml Tween-80, producing formulated antigen at a concentration of 118.5 mg/ml. Formulated FMP1 was sterile filtered with Millipak 40 0.22-um filtration unit and added to 3 ml vials for lyophilization. The vials were sealed with Lyo stoppers and metal crimps (BPR-334-01, Lot 0678)

Vaccine Potency

Female Balb/C mice were immunized subcutaneously with 100 ul of vaccine. Potency studies were performed with 1.0, 0.3 and 0.1 ug of MSP-$1_{42}$ in Adjuvant B (GlaxoSmithKline Biologicals, Rixensart, Belgium). The 10 ug dose was prepared with 10 ug of antigen and 100 ul of Adjuvant B and was used to make the 1.0 and 0.1 ug doses by diluting into 0.9% saline. Mice were primed and then bled and boosted four-weeks later, and bled again 2 weeks following boosting. Sera were analyzed by ELISA and results are reported in ELISA units, or the serum dilution that gives an absorbance of 1 OD 405 (Stoute et al., 1997, N. Engl. J. Med. 336, 86-91).

Seroconversion occurred if the following condition was met: (ELISA Units-3SD)post-vaccination−(ELISA Units+ 3SD)pre-vaccination>0

Safety and Immunogenicity

Rhesus monkeys were vaccinated intramuscularly with 50 ug of antigen formulated with ADJUVANT B or alum. Monkeys were boosted one, three, five, and seven months after priming and sera were collected prior to and two weeks following each immunization.

Serology

Sera were analyzed by IFA against methanol fixed 3D7 strain *P. falciparum* schizont-infected erythrocytes (Lyon et al., 1987, supra) and by kinetic ELISA. For this, the MSP-$1_{42}$ capture antigen was diluted in PBS at pH 7.4 and coated at 0.4 pmoles/well overnight at 4° C., and wells were blocked with CaseinBlock (Pierce). Sera were diluted 1:50,000 (ADJUVANT B) or 1:8,000 (Alum) in CaseinBlock and reacted for 1 h at room temperature, followed by reaction with alkaline phosphatase-conjugated rabbit anti-human IgG (H&L) (Promega) diluted 1:250 in CaseinBlock also for 1 hr at room temperature. Detection of p-nitrophenyl phosphate substrate conversion to product was measured at 5 min intervals for 30 min. The slope of the line was calculated by linear regression and R2 was at least 0.99 for each analysis.

Inhibition of Parasite Invasion

Rabbits were vaccinated four times subcutaneously with FMP1 in Freund's adjuvants and sera were collected three weeks after the final immunization. The IgG fractions of pre-immune and post-immune sera were prepared with Protein-G chromatography and quantified by using the Bradford Protein Determination assay (Pierce). For the invasion inhibition assay (Chulay et al., 1981, Am. J. Trop. Med. Hyg. 30, 12-19), the IgG fractions were dialyzed against RPMI 1640 adjusted to pH 7.4 with NaOH and added to settled 100 ul cultures of synchronous *P. falciparum* (3D7 strain) schizont-infected erythrocytes (3-5 nuclei) at 2% hematocrit and 0.25% parasitemia. In some experiments, native FMP1 or reduced and alkykated FMP1, dialyzed as above, were added as specificity controls to reverse the activity of inhibitory antibodies.

Example 1

Figure 1B:
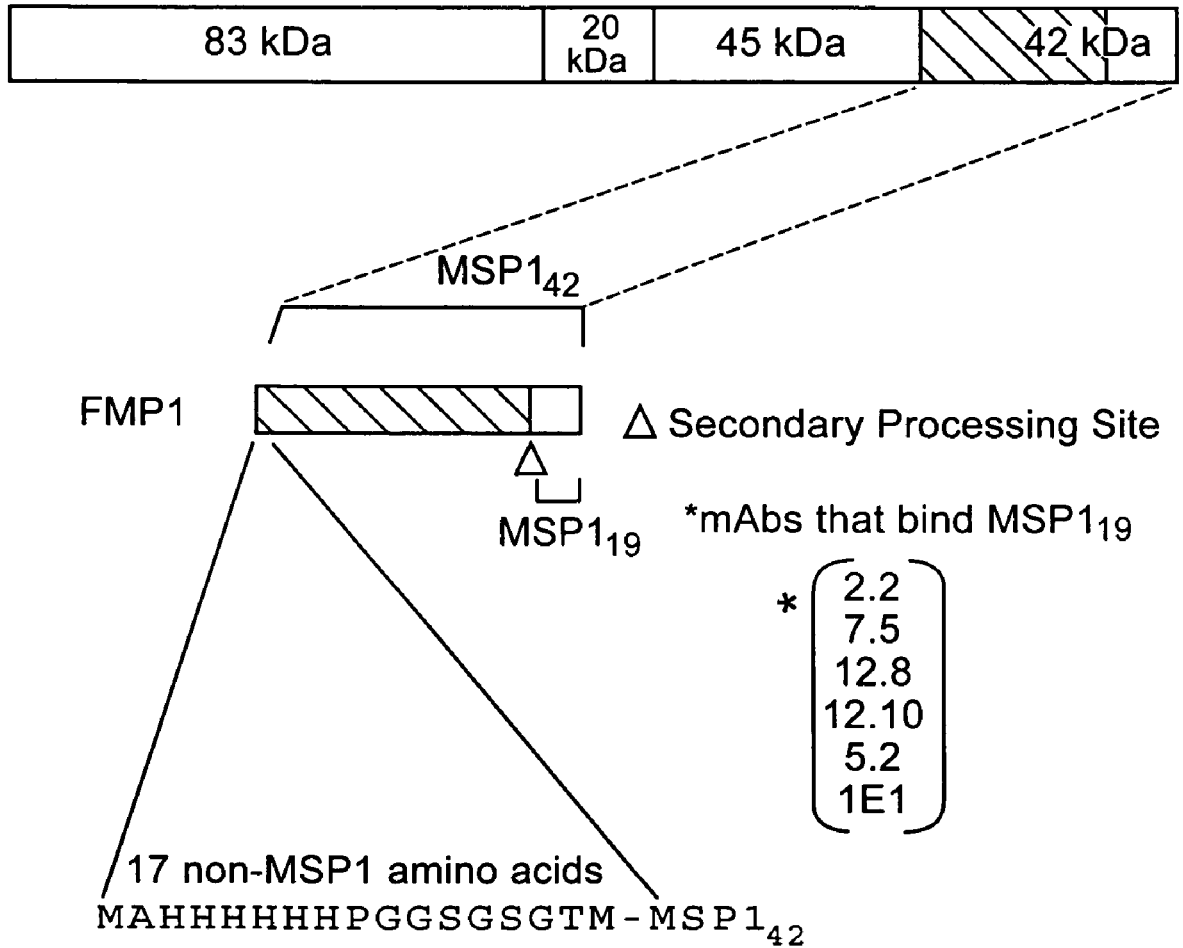
FIG. 1B: pET(AT)PfMSP-1$_{42}$ plasmid map. Inset shows the 17 non-MSP amino acids (the first 17 amino acid residues of SEQ ID NO:7).

The gene fragment containing *P. falciparum* 3D7 strain MSP-$1_{42}$ was cloned into pET32a (FIG. 1A) with several modifications. These included adding the gene for tetracycline, removing the trx gene and other elements, and adding a hexa-histidine affinity tag, which contained 17 non-MSP-$1_{42}$ amino acids fused to the N-terminus of MSP-$1_{42}$ (FIG. 1B). Our primary objective of expressing MSP-$1_{42}$ as a soluble protein in *E. coli* cytoplasm was achieved by systematically varying IPTG concentration and induction temperature. IPTG at 0.1 mM induced maximal protein synthesis and induction at 25° C. was required to express soluble protein (data not shown). The optimal biomass density for induction in 10 L fermentors was shown to be 4-6 OD600. These conditions were used to prepare GMP cell paste in a 300 L fermentor, and this paste was used to develop the purification process. The MSP-$1_{42}$ was purified by three chromatographic steps. After centrifugation, cleared lysates were applied to a $Ni^{+2}$-NTA Superflow resin for affinity purification (FIG. 2A, lane 1). This step removed most of the endotoxin, which depended on extensive washing of bound protein at low pH (pH 6.2) and high sodium chloride (500 mM). After this step, the protein was greater than 50% pure by densitometry (arrows show MSP-$1_{42}$ related bands). MSP-$1_{42}$ was purified to greater than 95% purity by chromatography on a Q-anion exchanger followed by a CM-cation exchanger (FIG. 2A, lanes 2 and 3 respectively). The Final Bulk Antigen (FMP1) was further characterized by SDS-PAGE under non-reducing and reducing conditions (FIG. 2B, lanes 1 and 2, respectively) and by immunoblotting with rabbit anti-*E. coli* antibody (FIG. 2C, lane 3) and MSP-1 specific mAbs. The MSP-$1_{33}$ specific mAb 7F1 reacted with two proteins migrating at 36 kD and 38 kD (FIG. 2C, lane 1), but the MSP-$1_{19}$ specific mAb 12.10 (FIG. 2C, lane 2) did not, nor did any of the other MSP-$1_{19}$ specific mAbs. Full-length MSP-$1_{42}$ (see FIG. 2) and all of the higher molecular weight aggregates were reactive against all the MSP-1 specific mAbs used. Long term stability studies showed that the FMP1 was stable when stored for 18 months at −80° C. but not when stored at 4° C. (degradation) or −20° C. (aggregation) (FIG. 3, lanes 1-3, respectively), compare with FIG. 2B (lane 1).

Example 2

Figure 4:
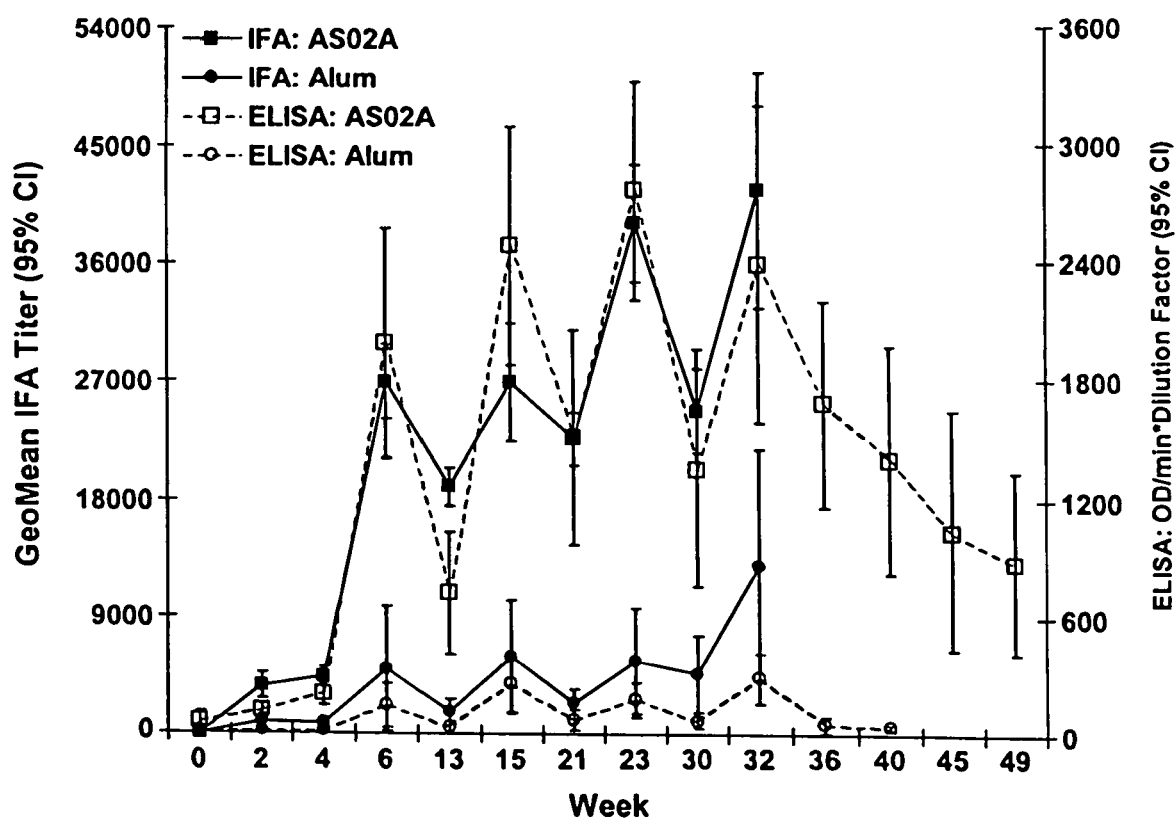
FIG. 4: FMP1 Immunogenicity. Rhesus monkeys were boosted 1, 3, 5, and 7 months after priming with FMP1/ADJUVANT B (rectangles) or FMP1/alum (circles). Sera were collected just prior to immunization (arrows) and two weeks after each immunization. In the case of the ADJUVANT B cohort serum collection continued monthly for 9 months. Antibody titers were measured by IFA (filled symbols) and kinetic ELISA (open symbols).
Figure 5:
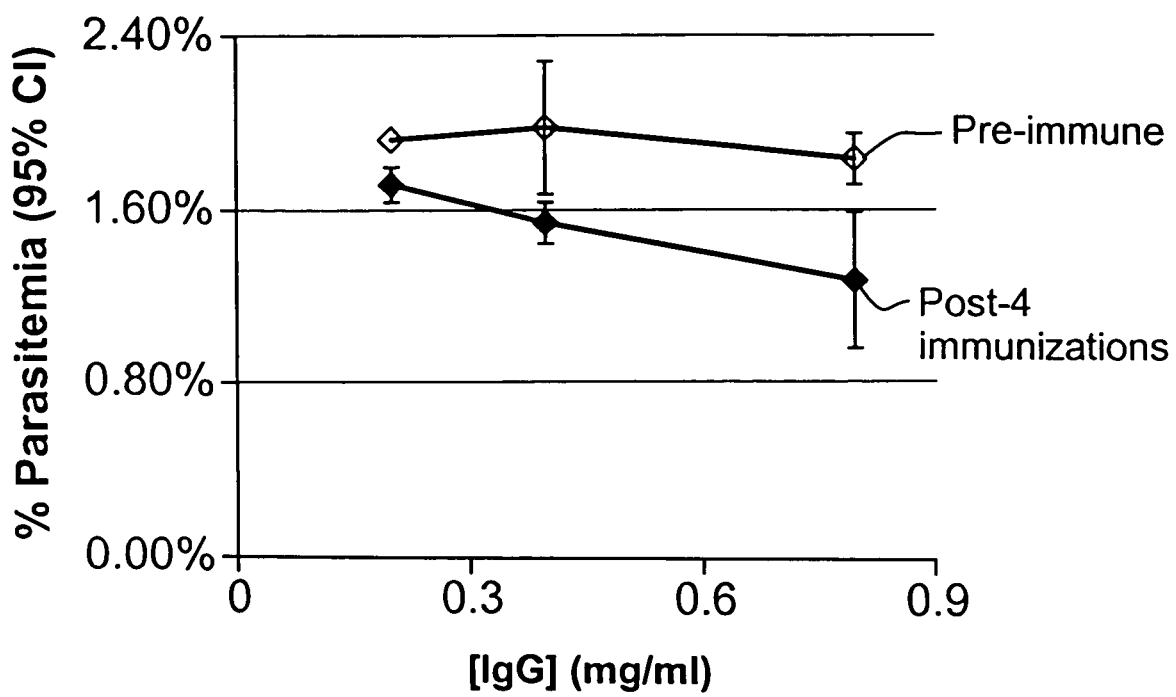
FIG. 5: Merozoite Invasion Inhibition. Triplicate synchronous cultures of *P. falciparum* schizont-infected erythrocytes were incubated for 24 hours with the IgG fractions of pre-immune (open diamonds) or immune (filled diamonds) IgG fractions from rabbits immunized with FMP1 in Fruends adjuvents. IgG was tested at doses of 200, 400, and 800 ug/ml and parasite growth was quantified by counting 5000 erythroctyes or 100 parasitized erythrocytes, whichever occurred first. Data are shown as the mean parasitemia and 95% confidence interval.

Vaccine potency studies were conducted in Balb/C mice immunized with FMP1 formulated for use with adjuvant ADJUVANT B. At the 0.3 ug and 1.0 ug doses, respectively, all mice seroconverted following one immunization. At the 0.1 ug dose 50% of the mice seroconverted following the first immunization; all seroconverted after the second (data not shown). Safety and immunogenicity of the product was assessed in Rhesus monkeys immunized up to five times with 50 ug doses of FMP1/ADJUVANT B (n=8) or FMP1/alum (n=6). No adverse local responses were observed and all biochemical and hematological laboratory tests were normal for both groups (not shown). FMP1/ADJUVANT B induced malaria parasite reactive IFA titers that increased to 1:28,000 by two weeks following the second immunization and maintained this level through the third immunization (FIG. 4, right ordinate). The fourth immunization induced a brief increase in titer, which returned to the 1:28,000 base within six weeks. The fifth immunization induced a response that was similar to the fourth. FMP1/alum induced IFA titer that paralleled those induced by FMP1/ADJUVANT B but were six-fold lower. FMP1/ADJUVANT B induced MSP-1$_{42}$-specific ELISA-reactive antibodies that increased to 2100 OD/min by two weeks following the second immunization and gradually increase to a maximum of 2800 OD/min after the fourth immunization (FIG. 4, left ordinate). The geometric mean antibody level after five immunizations was lower than after four, but this difference was not significant. By four weeks after each immunization antibody levels fell about 30% but stabilized after the third immunization. FMP1/alum induced ELISA-reactive antibodies levels roughly paralleled those induced by FMP1/ADJUVANT B but were about ten-fold lower. FMP1 in Freund's adjuvants induced invasion inhibitory IgG antibodies. The inhibition was titratible (FIG. 5) and was completely reversed by adding competing soluble FMP1 at a final concentration of 17 ug/ml and partially reversed by adding reduced and alkylated FMP1(approximately 50% reversal) at the same concentration (data not shown).

Example 3

FMP1 combined with the adjuvants ADJUVANT A, ADJUVANT B ADJUVANT C, ADJUVANT E, Adjuvant D, and Alum were assessed for safety and immunogenicity in Rhesus monkeys at the human dose of 50 ug/injection.

Studies were conducted in adult *Macaca mulatta* housed at the Armed Forces Research Institute of Medical Sciences (AFRIMS), Bangkok, Thailand. Monkeys were screened to exclude animals in poor health or with previous exposure to malaria, and were monitored for at least 6 weeks prior to the start of the study. Animals were randomly assigned to treatment groups, and vaccines were administered in a blinded standardized fashion while animals were under ketamine anesthesia.

Animals received intramuscular injections of FMP1 (50 ug) combined with adjuvant at 0, 4, 12 weeks. The attending veterinarian who conducted clinical and laboratory evaluations assessed vaccine safety. Blood was obtained for CBC and serum chemistries prior to administration and at 24, 48, and 72 hours immediately after each immunization. Local reactogenicity was monitored at the time of immunization, day 1, day 2, day 3, and day 14 post-immunization.

Safety

The following safety data apply to FMP1 combined with ADJUVANT B. The same data are available for the other adjuvants as well.

Clinical evaluations before and after each immunization revealed minimal local and no systemic toxicities. Reactogenicity of FMP1 in ADJUVANT B was assessed in each Rhesus monkey using the following criteria: 1) skin warmth or calor; 2) skin erythema or rubor; 3) skin swelling or edema; 4) muscle induration; 5) muscle necrosis. The intensity of the reactions were scored as follows: 0=none; 1=slight or mild reaction; 2=moderate reaction; 3=marked or severe reaction. The mean prevalence (Table 2A) and mean intensity (Table 2B) of local reactogenicity is given in the tables below. Erythema, skin swelling, and muscle induration were limited to the site of inoculation and resolved in all monkeys by 14 days post immunization. There were no cases of muscle necrosis. The intensity of muscle induration diminished daily from post immunization day 1 through day 3, and multiple immunizations did not increase the risk of adverse reactions. Behavior, activity, and food consumption remained normal.

TABLE 2A

Mean Prevalence of Reactogenicity- mean % positive (n = 8 Rhesus)

| Immunization Number | | Post-immunization day | Skin warmth/ calor | Skin erythema/ rubor | Skin swelling/ edema | Muscle induration | Muscle necrosis |
|---|---|---|---|---|---|---|---|
| 1 | 10 Aug. 1999 | — | 0% | 0% | 0% | 0% | 0% |
|   | 11 Aug. 1999 | 1 | 50% | 12.5% | 37.5% | 87.5% | 0% |
|   | 12 Aug. 1999 | 2 | 0% | 0% | 12.5% | 75% | 0% |
|   | 13 Aug. 1999 | 3 | 0% | 0% | 0% | 12.5% | 0% |
|   | 24 Aug. 1999 | 14 | 0% | 0% | 0% | 0% | 0% |
| 2 | 7 Sep. 1999 | — | 0% | 0 of 8 | 0 of 8 | 0 of 8 | 0% |
|   | 8 Sep. 1999 | 1 | 12.5% | 87.5% | 100% | 100% | 0% |
|   | 9 Sep. 1999 | 2 | 0% | 50% | 100% | 100% | 0% |
|   | 10 Sep. 1999 | 3 | 0% | 12.5% | 87.5% | 100% | 0% |
|   | 21 Sep. 1999 | 14 | 0% | 0% | 0% | 0% | 0% |
| 3 | 9 Nov. 1999 | — | 0 of 8 | 12.5% | 2 of 8 | 0 of 8 | 0% |
|   | 10 Nov. 1999 | 1 | 37.5% | 25% | 75% | 100% | 0% |
|   | 11 Nov. 1999 | 2 | 12.5% | 0% | 37.5% | 100% | 0% |
|   | 12 Nov. 1999 | 3 | 0% | 0% | 0% | 75% | 0% |
|   | 23 Nov. 1999 | 14 | 0% | 0% | 0% | 0% | 0% |

TABLE 2B

| Immunization Number | | Post-immunization day | Skin warmth/ calor | Skin erythema/ rubor | Skin swelling/ edema | Muscle induration | Muscle necrosis |
|---|---|---|---|---|---|---|---|
| 1 | 10 Aug. 1999 | — | 0 | 0 | 0 | 0 | 0 |
|   | 11 Aug. 1999 | 1 | 1 | 1 | 1.3 | 1.3 | 0 |
|   | 12 Aug. 1999 | 2 | 0 | 0 | 1 | 1 | 0 |
|   | 13 Aug. 1999 | 3 | 0 | 0 | 0 | 1 | 0 |
|   | 24 Aug. 1999 | 14 | 0 | 0 | 0 | 0 | 0 |

TABLE 2B-continued

| Immunization Number | | Post-immunization day | Skin warmth/ calor | Skin erythema/ rubor | Skin swelling/ edema | Muscle induration | Muscle necrosis |
|---|---|---|---|---|---|---|---|
| 2 | 7 Sep. 1999 | — | 0 | 0 | 0 | 0 | 0 |
|  | 8 Sep. 1999 | 1 | 2 | 1.6 | 3 | 2.9 | 0 |
|  | 9 Sep. 1999 | 2 | 0 | 1.8 | 3 | 2.4 | 0 |
|  | 10 Sep. 1999 | 3 | 0 | 1 | 2.6 | 2.3 | 0 |
|  | 21 Sep. 1999 | 14 | 0 | 0 | 0 | 0 | 0 |
| 3 | 9 Nov. 1999 | — | 0 | 0 | 0 | 0 | 0 |
|  | 10 Nov. 1999 | 1 | 1 | 1.5 | 1.3 | 2.1 | 0 |
|  | 11 Nov. 1999 | 2 | 1 | 0 | 1 | 1.6 | 0 |
|  | 12 Nov. 1999 | 3 | 0 | 0 | 0 | 1.5 | 0 |
|  | 23 Nov. 1999 | 14 | 0 | 0 | 0 | 0 | 0 |

Mean laboratory values for the entire group (Tables 3 and data not shown) indicated no significant abnormalities or trends in hematologic or biochemical laboratory tests. Quantitative platelet counts varied before and after immunization. This variation occurred both within individual Rhesus monkeys and between Rhesus. All blood prior to December 1999 was collected in heparin anti-coagulant, and we suspected that the platelet count variation was attributed to the use of the heparin anticoagulant. All Rhesus in the study had blood samples collected in mid December 1999 using both heparin and EDTA anticoagulants and quantitative platelet counts determined at 2 locations in Bangkok Thailand. AFRIMS veterinary pathologists read all blood smears from August, September, and November and the platelet counts were read as adequate, increased, or decreased. It was decided that all further hematologic (CBC) laboratory assays would be collected in EDTA. The January 2000 samples reflect this change in blood collection procedure with normal platelet counts observed in all Rhesus immunized with FMP1 and ADJUVANT B days 1, 2, and 3 following a $4^{th}$ immunization. In addition, all blood smears at each time point reviewed after immunizations 1, 2, and 3 had adequate platelet counts (data not shown).

Immunogenicity

Humoral Immunity: FMP1 combined with ADJUVANT A or ADJUVANT B induced similar levels of ELISA (Table 4A) and IFA (Table 4B) reactive antibody and were significantly more potent than the other adjuvant combinations. FMP1 combined with Alum was the least immunogenic by ELISA after two immunizations, but was not different from ADJUVANT C, ADJUVANT E and Adjuvant D by ELISA after the third immunization. FMP1 combined with Alum or with ADJUVANT C induced similar levels of IFA reactive antibody and induced significantly more IFA reactive antibody than FMP1 combined with ADJUVANT E or Adjuvant D.

Cellular Immunity: FMP1 combined with ADJUVANT A or ADJUVANT B induced different cytokine response profiles (Table 5). Both vaccines induced comparable levels of IFN-γ response after the $3^{rd}$ dose, however, the IL-5 response was greatly suppressed in animals receiving FMP1 combined with ADJUVANT A. Duration of T cell response data indicate that IFN-γ response generated by FMP1 combined with both ADJUVANT A and ADJUVANT B persists at least 24 weeks after vaccination. The difference on Th1/Th2 polarization of FMP1 formulated with ADJUVANT B and ADJUVANT A was not anticipated.

TABLE 3

Mean Biochemical Laboratory Test Values

| | Immunization #1 August | | | | Immunization #2 September | | | | Immunization #3 November | | | |
|---|---|---|---|---|---|---|---|---|---|---|---|---|
| | 5 | 11 | 12 | 13 | 7 | 8 | 9 | 10 | 9 | 10 | 11 | 12 |
| BUN (mg/ml) | | | | | | | | | | | | |
| MEAN | 19.7 | 17.3 | 18.1 | 19.0 | 20.0 | 16.9 | 20.6 | 17.9 | 17.9 | 18.5 | 16.3 | 16.4 |
| s.d. | 3.5 | 3.4 | 2.4 | 3.7 | 2.9 | 2.6 | 2.2 | 2.9 | 2.9 | 1.1 | 2.4 | 1.9 |
| CREATININE (mg/ml) | | | | | | | | | | | | |
| MEAN | 0.76 | 0.81 | 0.80 | 0.81 | 0.80 | 0.83 | 0.75 | 0.81 | 0.88 | 0.90 | 0.83 | 0.86 |
| s.d. | 0.07 | 0.04 | 0.11 | 0.06 | 0.09 | 0.12 | 0.08 | 0.11 | 0.18 | 0.09 | 0.10 | 0.12 |
| AST (U/l) | | | | | | | | | | | | |
| MEAN | 23.9 | 80.8 | 67.9 | 61.9 | 27.4 | 47.0 | 50.1 | 47.6 | 27.8 | 68.8 | 57.3 | 46.0 |
| s.d. | 3.7 | 38.9 | 22.5 | 24.4 | 4.1 | 13.6 | 20.3 | 17.1 | 4.5 | 23.3 | 18.5 | 14.9 |
| ALT (U/l) | | | | | | | | | | | | |
| MEAN | 28.0 | 50.9 | 50.1 | 56.3 | 32.8 | 37.3 | 39.5 | 43.9 | 38.4 | 41.5 | 47.0 | 51.5 |
| s.d. | 9.1 | 16.0 | 15.2 | 17.1 | 13.3 | 13.6 | 12.7 | 12.9 | 10.6 | 13.7 | 12.8 | 13.5 |
| CPK (U/l) | | | | | | | | | | | | |
| MEAN | 301 | 1192 | 879 | 923 | 256 | 791 | 671 | 470 | 307 | 2443 | 915 | 520 |
| s.d. | 239 | 550 | 684 | 657 | 208 | 356 | 298 | 237 | 368 | 1039 | 721 | 221 |

TABLE 4A

Rhesus Humoral Responses to FMP1 formulated with various adjuvants

| | | Midpoint ELISA Titer | | | | | |
|---|---|---|---|---|---|---|---|
| | | Week 0* | Week 2 | Week 4* | Week 6 | Week 13* | Week 15 |
| ADJUVANT A | GMT | 13 | 1402 | 1824 | 52161 | 9291 | 74348 |
| | 95% CI | 17 | 1413 | 1171 | 15783 | 4088 | 20937 |
| ADJUVANT B | GMT | 7 | 2439 | 3929 | 87096 | 25574 | 98458 |
| | 95% CI | 2 | 657 | 2164 | 24748 | 6797 | 42826 |
| ADJUVANT C | GMT | 27 | 325 | 715 | 31654 | 2576 | 25120 |
| | 95% CI | 101 | 597 | 714 | 15885 | 633 | 9183 |
| ADJUVANT E | GMT | 6 | 80 | 186 | 25360 | 2698 | 35945 |
| | 95% CI | 3 | 155 | 234 | 9517 | 915 | 10550 |
| ADJUVANT D | GMT | 5 | 245 | 392 | 16899 | 1799 | 23647 |
| | 95% CI | 24 | 315 | 259 | 16810 | 2113 | 12386 |
| Alum | GMT | 8 | 64 | 98 | 5501 | 751 | 10969 |
| | 95% CI | 21 | 129 | 118 | 7168 | 865 | 11011 |

*Immunization time point

TABLE 4B

| | | Endpoint IFA Titer | | | | | |
|---|---|---|---|---|---|---|---|
| | | Week 0* | Week 2 | Week 4* | Week 6 | Week 13* | Week 15 |
| ADJUVANT A | GMT | 0 | 4000 | 1308 | 26251 | 11888 | 43069 |
| | 95% CI | 0 | 2079 | 7492 | 5410 | 6372 | 11853 |
| ADJUVANT B | GMT | 0 | 3668 | 4362 | 26909 | 19027 | 26909 |
| | 95% CI | 0 | 1283 | 1793 | 5132 | 6584 | 5132 |
| ADJUVANT C | GMT | 0 | 24 | 917 | 9514 | 2594 | 10375 |
| | 95% CI | 488 | 257 | 849 | 6458 | 0 | 6187 |
| ADJUVANT E | GMT | 14 | 12 | 15 | 144 | 31 | 257 |
| | 95% CI | 3 | 4 | 6 | 98 | 29 | 131 |
| ADJUVANT D | GMT | 50 | 54 | 74 | 675 | 169 | 844 |
| | 95% CI | 13 | 19 | 21 | 319 | 66 | 238 |
| Alum | GMT | 0 | 316 | 794 | 2828 | 1414 | 4490 |
| | 95% CI | 0 | 470 | 0 | 4158 | 839 | 3719 |

*Immunization time point

TABLE 5

Polarization by ADJUVANT A of Immune Rosponses to FMP1

| Adjuvant | IFN-γ/IL-5 |
|---|---|
| ADJUVANT A | 4.2 |
| ADJUVANT B | 0.75 |
| ADJUVANT C | 2.3 |
| ADJUVANT E | 0.77 |
| Adjuvant D | 5.0 |
| Alum | 0.53 |

Example 4

A Phase I dose escalation clinical trial of the recombinant *Plasmodium falciparum* malaria vaccine candidate FMP1/ADJUVANT B was recently completed at the Walter Reed Army Institute of Research (WRAIR) in Silver Spring, Md. in 15 adult human volunteers to assess safety, reactogenicity, and immunogenicity. This vaccine was created by researchers at the WRAIR and manufactured at the Pilot Bioproduction Facility at WRAIR. In the initial Phase I clinical trial conducted during 4th quarter 2000—1st quarter 2001, three groups of 5 volunteers were immunized with ⅕th dose, ½ dose, or full dose of vaccine at 0, 1, and 3 months. Tables 1 and 2 below summarize the demographics of the study population.

Safety and Adverse Events:

Local and general systemic adverse events were assessed at 6 time points following each immunization, and blood tests to evaluate hematologic, renal, and hepatic abnormalities were performed before and after each immunization. The vaccine proved safe in all 15 volunteers with NO serious adverse events or clinical laboratory abnormalities noted. There were no drop-outs from the vaccine trial. All adverse events were graded according to severity. There were no Serious Adverse Events (SAE's) requiring hospitalization nor were there any grade 3 adverse events as defined below. Grade "3"=Adverse experience which prevents normal everyday activities and necessitates a corrective therapy. The specific occurances by subject and by dose of all adverse events are summarized in tables 3-7 below. In summary, the most frequent adverse events was minimal pain at the site of vaccine injection which disappeared by 24 hours post-inoculation.

Immunogenicity:

ELISA:

The vaccine was extremely potent in inducing high-titer antibody responses in all volunteers as assessed by ELISA (enzyme-linked immunoabsorbent assay). The table below summarizes the mean, standard deviation, and geometric mean antibody titers for each of the three vaccine groups.

TABLE 6

ANTIBODY TITERS to MSP-$1_{42}$ BY ELISA
VALUES INDICATE DILUTION OF SERA WHICH GIVES OD = 1

|  | Day 0 | Day 14 | Day 28 | Day 42 | Day 84 | Day 98 |
|---|---|---|---|---|---|---|
| ⅕ Dose |  |  |  |  |  |  |
| Average | 12 | 312 | 462 | 18066 | 7371 | 32648 |
| Std Dev | 8 | 191 | 236 | 8406 | 6304 | 24046 |
| Geo Mean | 10 | 272 | 412 | 16440 | 5749 | 26626 |
| ½ DOSE |  |  |  |  |  |  |
| Average | 28 | 1285 | 2530 | 44172 | ND | 57771 |
| Std Dev | 6 | 1882 | 2631 | 21176 | ND | 24192 |
| Geo Mean | 28 | 636 | 1762 | 40744 | ND | 53569 |
| Full Dose |  |  |  |  |  |  |
| Average | 32 | 688 | 990 | 32461 | 15914 | 50053 |
| Std Dev | 32 | 414 | 306 | 19307 | 5650 | 29991 |
| Geo Mean | 22 | 586 | 951 | 28448 | 14938 | 42799 |

IFA: The vaccine was also immunogenic as assessed by indirect immunofluorescence titers to malaria parasites.

TABLE 7

IMMUNOFLUORESCENCE to 3D7 Parasites
Values indicate serum dilution which gives 1 + IFA
intensity to methanol-fixed malaria parasites

DAY OF STUDY

|  | Day 0 | Day 14 | Day 28 | Day 42 | Day 84 | Day 98 |
|---|---|---|---|---|---|---|
| ⅕ Dose- GROUP 1 |  |  |  |  |  |  |
| Geomean | 200 | 200 | 200 | 1393 | 2111 | 3676 |
| 95% CI |  |  |  | 1152 | 2533 | 5155 |
| SD | 0 | 0 | 0 | 1315 | 2890 | 5881 |
| ½ Dose- GROUP 2 |  |  |  |  |  |  |
| Geomean | 200 | 200 | 200 | 2425 | ND | 5572 |
| 95% CI |  |  |  | 768 | ND | 1254 |
| SD | 0 | 0 | 0 | 876 | ND | 1431 |
| Full Dose- GROUP 3 |  |  |  |  |  |  |
| Geomean | 200 | 200 | 200 | 3200 | 3676 | 8445 |
| 95% CI |  |  |  | 1536 | 1882 | 3967 |
| SD | 0 | 0 | 0 | 1753 | 2147 | 4525 |

Figures 6A, 6B, 6C:
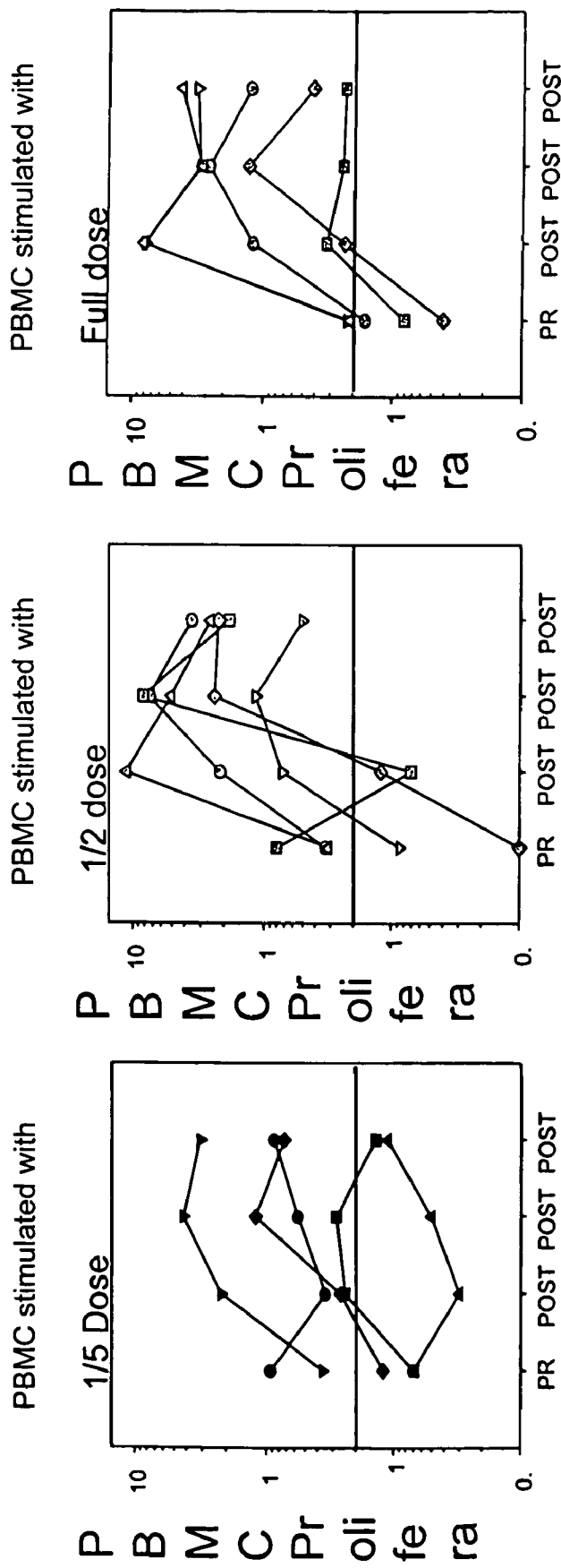

In addition, cell-mediated immunologic responses were noted in the majority of vaccinated subjects. Peripheral blood mononuclear cells were stimulated with MSP-1 antigen or *P. falciparum* parasitized erythrocytes and proliferation was measured by uptake of $^3$H-thymidine. FIG. 6 shows the results of PBMC proliferation in each of the subjects after each dose of vaccine.

Summary

In this initial clinical trial involving a small number of volunteers, FMP1/ADJUVANT B has been shown to be a safe and highly immunogenic vaccine that elicits both parasite-reactive antibodies and cellular responses. This study develops a foundation to further test its safety profile and evaluate its efficacy to reduce morbidity and mortality in target populations directly affect by *P. falciparum* malaria.

Safety Data

TABLE 8

Number of subjects

|  | TOTAL | Percent | Group 1 | Group 2 | Group 3 |
|---|---|---|---|---|---|
| Number of subjects planned | 15 | 100% | 5 | 5 | 5 |
| Subjects or vaccine number not allocated | 0 | 0 | 0 | 0 | 0 |
| Number of subjects enrolled (Total cohort) | 15 | (100%) | 5 | 5 | 5 |

"Reasons for elimination . . ."
Group 1: FMP1/ADJUVANT B: ⅕sth dose
Group 2: FMP1/ADJUVANT B: ½ dose
Group 3: FMP1/ADJUVANT B: full dose

TABLE 9

Demographics: Study population

| Sex | N | Mean Age (years) | Min age (years) | Max. Age (years) | S.D. (years) |
|---|---|---|---|---|---|
| Female | 5 | 32.2 | 27 | 51 | 10.8 |
| Male | 10 | 34.4 | 22 | 52 | 11.1 |
| Total | 15 | 33.7 | 22 | 52 | 10.7 |

N = total number of subjects
S.D. = standard deviation

TABLE 10

Incidence and nature of symptoms reported per dose and per subject after vaccination

|  |  | General symptoms | | Local symptoms | |
|---|---|---|---|---|---|
| Dose | Group N | n | % | n | % |
| By dose |  |  |  |  |  |
| Dose 1 | 15 | 2 | 13 | 12 | 80 |
| Dose 2 | 15 | 2 | 13 | 11 | 73 |
| Dose 3 | 15 | 1 | 7 | 10 | 67 |
| Overall | 45 | 5 | 11 | 33 | 73 |
| By volunteer |  |  |  |  |  |
| Group 1 | 5 | 1 | 20 | 4 | 80 |
| Group 2 | 5 | 1 | 20 | 4 | 80 |
| Group 3 | 5 | 2 | 40 | 5 | 100 |

N per dose = Number of documented doses
N per volunteer = Number of volunteers
n per dose = Number of documented doses with at least one symptom
n per subject = Number of subjects with at least one documented dose

TABLE 11

Incidence of solicited local symptoms including symptoms graded at maximum intensity

| Solicited local | | Group 1 (N = 15) | | Group 2 (N = 15) | | Group 3 (N = 15) | |
|---|---|---|---|---|---|---|---|
| Symptom | Intensity | n | % | n | % | n | % |
| Pain | Total | 8 | 53.3 | 11 | 73.3 | 14 | 93.3 |
|  | grade "3" | 0 | 0 | 0 | 0 | 0 | 0 |
| Redness | Total | 1 | 6.7 | 4 | 26.7 | 2 | 13.3 |
|  | >50 mm/>24 h | 0 | 0 | 0 | 0 | 0 | 0 |

TABLE 11-continued

Incidence of solicited local symptoms including symptoms graded at maximum intensity

| Solicited local | | Group 1 (N = 15) | | Group 2 (N = 15) | | Group 3 (N = 15) | |
|---|---|---|---|---|---|---|---|
| Symptom | Intensity | n | % | n | % | n | % |
| Swelling | Total | 0 | 0 | 0 | 0 | 0 | 0 |
|  | >50 mm/>24 h | 0 | 0 | 0 | 0 | 0 | 0 |

Group 1: FMP1/ADJUVANT B: ⅕th dose
Group 2: FMP1/ADJUVANT B: ½ dose
Group 3: FMP1/ADJUVANT B: full dose
N = Total number of documented doses
n = number of documented doses after which there is at least one report of a symptom
% = percentage of documented doses after which there is at least one report of a symptom
Grade "3" = pain preventing normal daily activity and necessitates a corrective therapy
>50 mm/>24 h = redness or swelling with a diameter of more than 50 mm and persisting for more than 24 hours

TABLE 12

Subjects reporting solicited local symptoms including symptoms graded at maximum intensity

| Solicited local | | Group 1 (N = 5) | | Group 2 (N = 5) | | Group 3 (N = 5) | |
|---|---|---|---|---|---|---|---|
| symptom | Intensity | n | % | n | % | n | % |
| Pain | Total | 4 | 80 | 4 | 80 | 5 | 100 |
|  | grade "3" | 0 | 0 | 0 | 0 | 0 | 0 |
| Redness | Total | 1 | 20 | 3 | 60 | 2 | 40 |
|  | >50 mm/>24 h | 0 | 0 | 0 | 0 | 0 | 0 |
| Swelling | Total | 0 | 0 | 0 | 0 | 0 | 0 |
|  | >50 mm/>24 h | 0 | 0 | 0 | 0 | 0 | 0 |

Group 1: FMP1/ADJUVANT B: ⅕th dose
Group 2: FMP1/ADJUVANT B: ½ dose
Group 3: FMP1/ADJUVANT B: full dose
N = Total number of subjects
n = number of subjects reporting at least one report of a symptom
% = percentage of subjects reporting at least symptom
Grade "3" = pain preventing normal daily activity and necessitates a corrective therapy
>50 mm/>24 h = redness or swelling with a diameter of more than 50 mm and persisting for more than 24 hours

TABLE 13

Incidence of solicited general symptoms including symptoms graded at maximum intensity and those probably or suspected of being related to vaccination

| | | Group 1 N = 15 | | Group 2 N = 15 | | Group 2 N = 15 | |
|---|---|---|---|---|---|---|---|
| Symptoms | | N | % | N | % | N | % |
| Arthralgia | Total | 0 | 0 | 0 | 0 | 1 | 6.7 |
|  | PB/SU | 0 | 0 | 0 | 0 | 0 | 0 |
|  | PB/SU & Grade "3" | 0 | 0 | 0 | 0 | 0 | 0 |
| Fever | Total | 0 | 0 | 0 | 0 | 1 | 6.7 |
|  | PB/SU | 0 | 0 | 0 | 0 | 0 | 0 |
|  | PB/SU & Grade "3" | 0 | 0 | 0 | 0 | 0 | 0 |
| Headache | Total | 0 | 0 | 0 | 0 | 0 | 0 |
|  | PB/SU | 0 | 0 | 0 | 0 | 0 | 0 |
|  | PB/SU & Grade "3" | 0 | 0 | 0 | 0 | 0 | 0 |
| Malaise | Total | 1 | 6.7 | 1 | 6.7 | 1 | 6.7 |
|  | PB/SU | 1 | 6.7 | 1 | 6.7 | 0 | 0 |
|  | PB/SU & Grade "3" | 0 | 0 | 0 | 0 | 0 | 0 |
| Myalgia | Total | 1 | 6.7 | 0 | 0 | 1 | 6.7 |
|  | PB/SU | 1 | 6.7 | 0 | 0 | 0 | 0 |
|  | PB/SU & Grade "3" | 0 | 0 | 0 | 0 | 0 | 0 |
| Rash | Total | 0 | 0 | 0 | 0 | 0 | 0 |
|  | PB/SU | 0 | 0 | 0 | 0 | 0 | 0 |
|  | PB/SU & Grade "3" | 0 | 0 | 0 | 0 | 0 | 0 |
| Dizziness | Total | 0 | 0 | 0 | 0 | 1 | 6.7 |
|  | PB/SU | 0 | 0 | 0 | 0 | 0 | 0 |
|  | PB/SU & Grade "3" | 0 | 0 | 0 | 0 | 0 | 0 |
| Nausea | Total | 0 | 0 | 0 | 0 | 1 | 6.7 |
|  | PB/SU | 0 | 0 | 0 | 0 | 0 | 0 |
|  | PB/SU & Grade "3" | 0 | 0 | 0 | 0 | 0 | 0 |

Group 1: FMP1/ADJUVANT B: ⅕th dose
Group 2: FMP1/ADJUVANT B: * dose
Group 3: FMP1/ADJUVANT B: full dose
N = Total number of documented doses.
n = number of documented doses after which there is at least one report of a symptom.
% = percentage of documented doses after which there is at least one report of a symptom.
Grade "3" = Adverse experience which prevents normal everyday activities and necessitates a corrective therapy.
PB/SU = Probably or suspected of an association.

TABLE 14

Subjects reporting solicited general symptoms including symptoms graded at maximum intensity and those probably or suspected of being related to vaccination

| | | Group 1 (⅕ dose) N = 5 | | Group 2 (½ dose) N = 5 | | (Full dose) Group 2 N = 5 | |
|---|---|---|---|---|---|---|---|
| Symptoms | | N | % | N | % | N | % |
| Arthralgia | Total | 0 | 0 | 0 | 0 | 1 | 20 |
|  | PB/SU | 0 | 0 | 0 | 0 | 0 | 0 |
|  | PB/SU & Grade "3" | 0 | 0 | 0 | 0 | 0 | 0 |
| Fever | Total | 0 | 0 | 0 | 0 | 1 | 20 |
|  | PB/SU | 0 | 0 | 0 | 0 | 0 | 0 |
|  | PB/SU & Grade "3" | 0 | 0 | 0 | 0 | 0 | 0 |
| Headache | Total | 0 | 0 | 0 | 0 | 0 | 0 |
|  | PB/SU | 0 | 0 | 0 | 0 | 0 | 0 |
|  | PB/SU & Grade "3" | 0 | 0 | 0 | 0 | 0 | 0 |
| Fatigue | Total | 1 | 20 | 1 | 20 | 1 | 20 |
|  | PB/SU | 1 | 20 | 1 | 20 | 0 | 0 |
|  | PB/SU & Grade "3" | 0 | 0 | 0 | 0 | 0 | 0 |
| Myalgia | Total | 1 | 20 | 0 | 0 | 1 | 20 |
|  | PB/SU | 1 | 20 | 0 | 0 | 0 | 0 |
|  | PB/SU & Grade "3" | 0 | 0 | 0 | 0 | 0 | 0 |

TABLE 14-continued

Subjects reporting solicited general symptoms including symptoms graded at maximum intensity and those probably or suspected of being related to vaccination

| Symptoms | | Group 1 (1/5 dose) N = 5 | | Group 2 (1/2 dose) N = 5 | | (Full dose) Group 2 N = 5 | |
|---|---|---|---|---|---|---|---|
| | | N | % | N | % | N | % |
| Rash | Total | 0 | 0 | 0 | 0 | 0 | 0 |
| | PB/SU | 0 | 0 | 0 | 0 | 0 | 0 |
| | PB/SU & Grade "3" | 0 | 0 | 0 | 0 | 0 | 0 |
| Dizziness | Total | 0 | 0 | 0 | 0 | 1 | 20 |
| | PB/SU | 0 | 0 | 0 | 0 | 0 | 0 |
| | PB/SU & Grade "3" | 0 | 0 | 0 | 0 | 0 | 0 |
| Nausea | Total | 0 | 0 | 0 | 0 | 1 | 20 |
| | PB/SU | 0 | 0 | 0 | 0 | 0 | 0 |
| | PB/SU & Grade "3" | 0 | 0 | 0 | 0 | 0 | 0 |

N = Total number of subjects.
n = number of subject reporting at least one report of a symptom.
% = percentage of subject reporting at least one report of a symptom.
Grade "3" = Adverse experience which prevents normal everyday activities and necessitates a corrective therapy.
PB/SU = Probably or suspected of an association.

Example 5

Three rabbits per immunization group were vaccinated 4 times at 3-week intervals with 50 μg FMP1 (3D7) in Montanide adjuvant, subcutaneously, or with FMP1 in ADJUVANT B, intramuscularly. Two negative control rabbits per group were immunized with each adjuvant alone. A final control rabbit was immunized with reduced and alkylated MSP1$_{42}$ (3D7) in Montanide. Each rabbit was bled from the ear vein 2 weeks following each immunization. Following the fourth immunization the rabbits were ex-sanguinated from the heart and the sera from these rabbits was analyzed by MSP1 (3D7)-specific antigen ELISA's.

The sera were analyzed by MSP1 (3D7)-specific ELISA and by kinetic ELISA. The MSP1-specific capture antigen was diluted in PBS at pH 7.4 and coated at 0.4 pmoles/well overnight at 4° C. and the wells were blocked with Casein-Block (Pierce). Sera were first diluted by 1:25 and then followed by two-fold serial dilutions down the plate up to 1.6× $10^6$ fold. Sera were reacted for 1 hour at room temperature, followed by reaction with alkaline phosphatase-conjugated goat anti-rabbit IgG (H&L)(Promega) diluted 1:5,000 in CaseinBlock for 1 hour at room temperature. Detection of p-nitrophenyl phosphate substrate conversion to product was measured at 60 minutes. The data are reported as the average of triplicate values plotted from the titration curve measured at $OD_{405}$.

Immunization with FMP1 in Montanide and FMP1 in ADJUVANT B induces high MSP1$_{42}$ specific antibody titers following the second immunization. The geometric mean of the post fourth immunization MSP1$_{42}$ specific antibody titers induced by immunization with FMP1/ADJUVANT B and FMP1/Montanide were 1:363,000 and 1:182,000, respectively. Neither adjuvant/antigen combination substantially boosted the MSP1$_{42}$ specific antibody titers after a third and fourth immunization.

Discussion

Here we describe the development, fermentation, expression, purification and characterization of a safe and immunogenic recombinant MSP-1$_{42}$ that is suitable for production of antibodies and for use in diagnostic assays and as a potential vaccine.

Figure 3:
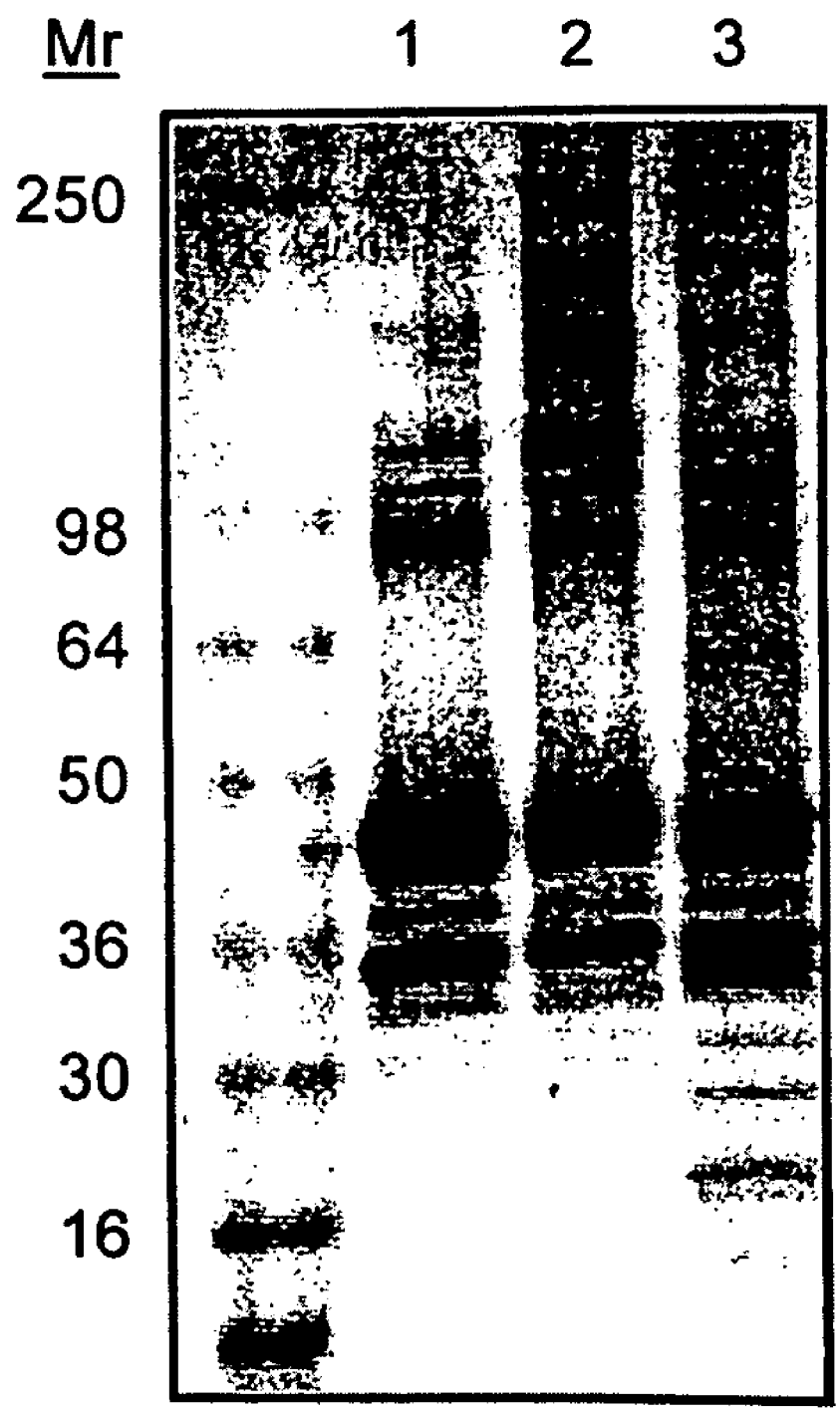
FIG. 3: FMP1 Stability. Commassie Blue stained non-reduced SDS-PAGE gel with 10 ug samples of FMP1 stored for 18 months under various conditions. Lane 1, –80° C.; lane 2, –20° C.; lane 3, 4° C.

MSP-1$_{42}$ which was derived from recombinant E. coli was highly purified and met all FDA standards necessary for testing safety and immunogenicity in humans. Endotoxin levels were significantly below the FDA acceptable levels (FDA; 350 EU/dose/70 kg human, Our Process; 9.14 EU/dose/70 kg human). Residual levels of all chemicals used in the purification process were quantified and determined to be within levels set as production specifications. Although the MSP-1$_{42}$ comprised greater than 95% of the protein in the final product, it was not homogeneous due to proteolysis at the C-terminal end of the protein. This proteolysis appeared to occur during expression in the E. coli host because long term studies showed that the antigen was stable when stored at −80° C. for 18 months, revealing little change in the Coomassie Blue staining pattern or mAb reaction patterns in immunoblots (FIG. 3).

Previous studies have shown that the induction of antibody responses to epitopes on MSP-1$_{19}$ correlate with clinical immunity to malaria (Egan et al., 1996, J. Infect. Dis. 173, 765-769), suggesting that induction of such responses depends on correctly forming the disulfide-dependent conformational epitopes present within the MSP-1$_{19}$ portion of MSP-1$_{42}$. This conclusion is further supported by the observation that the only MSP-1$_{19}$ specific mAbs capable of inhibition merozoite invasion react with conformational epitopes (Burghaus et al., 1994, Mol. Biochem. Parasitol. 64, 165-169). Recombinant MSP-1$_{42}$ has correct structure because it reacted with all of the MSP-1$_{19}$ specific mAbs we used; these were raised against malaria parasites and included functional mAbs classified as growth or invasion inhibitory (mAb 12.10, 12.8) (Blackman et al., 1990, supra) and blocking inhibitory mAbs (mAb 7.5, 2.2, 1E1) (Guevara et al., 1997, J. Exp. Med. 186, 1689-1699).

These data support the continued use of bacterial systems for expressing soluble malaria antigens that contain conformational epitopes as potential vaccine candidates.

In addition, FMP1/ADJUVANT B was highly immunogenic in the Rhesus monkeys as well as Balb/C mice. After three immunizations the geometric mean IFA antibody titers induced in Rhesus monkeys exceeded 1:36,000 and the geometric mean ELISA titer exceed 26,000 OD/min (FIG. 4); these titers did not change with further immunization. FMP1/ADJUVANT B induced approximately six times more MSP-1 specific antibodies than FMP1/Alum (FIG. 4). MSP-1 specific antibodies induced by FMP1 were predominantly against MSP-1$_{42}$ and MSP-1$_{19}$ compared to MSP-1$_{33}$ (not shown). This result, when taken in combination with FMP1's ability to induce high titer antibodies that react with schizont-infected erythrocytes and it's ability to induce invasion inhibitory antibodies (FIG. 5 and Table 1) further indicates that it has correct structure. Currently, the only malaria vaccine that has reproducibly protected human volunteers is the RTS,S/ADJUVANT B vaccine (Kester et al., 2001, J. Infect. Dis. 183, 640-647). When combined with ADJUVANT B, FMP1 was highly immunogenic and caused no adverse biochemical or local reactions in mice.

What is claimed is:

1. A recombinant vector comprising a DNA sequence from *Plasmodium falciparum* 3D7 encoding a C-terminal 42 kD fragment of merozoite surface protein-1 MSP-1 set forth as SEQ ID NO:7, wherein expression of said vector under suitable conditions results in a protein that retains its native folding.

2. An isolated host cell transformed with the vector according to claim 1.

3. The host cell of claim 2 wherein said host is *E. coli* BL21 (DE3).

4. A method for producing and purifying recombinant *P. falciparum* MSP-1$_{42}$ protein comprising:

growing a host cell containing a vector of claim 1 expressing MSP-1$_{42}$ proteins from *P. falciparum* 3D7 in a suitable culture medium, causing expression of said vector under suitable conditions for production of soluble MSP-1$_{42}$ protein and, lysing said host cells and recovering said MSP-1$_{42}$ protein such that it retains its native folding.

5. The method of claim 4 wherein said expression of said vector is by induction with IPTG at a temperature range of 24° C.-27° C.

6. The method of claim 5 wherein said induction is at 25° C.

7. The method of claim 4 wherein lysing of cells is in the presence of imidazole.

8. The method of claim 4 further comprising removal of *E. coli* endotoxin.

9. The method of claim 8 wherein said removal of endotoxin is by application to a Ni-NTA column.

* * * * *

UNITED STATES PATENT AND TRADEMARK OFFICE
CERTIFICATE OF CORRECTION

PATENT NO. : 7,595,191 B2  
APPLICATION NO. : 11/039880  
DATED : September 29, 2009  
INVENTOR(S) : Lyon et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 841 days.

Signed and Sealed this

Twenty-eighth Day of September, 2010

David J. Kappos  
*Director of the United States Patent and Trademark Office*

SEQUENCE LISTING

<160> NUMBER OF SEQ ID NOS: 12

<210> SEQ ID NO 1
<211> LENGTH: 546
<212> TYPE: PRT
<213> ORGANISM: Artificial sequence
<220> FEATURE:
<223> OTHER INFORMATION: E. coli expressed P. falciparum MSP142 (3D7)
    Protein Sequence in pET-Trx42

<400> SEQUENCE: 1

```
Met Ser Asp Lys Ile Ile His Leu Thr Asp
 1               5                  10

Asp Ser Phe Asp Thr Asp Val Leu Lys Ala
                15                  20

Asp Gly Ala Ile Leu Val Asp Phe Trp Ala
                25                  30

Glu Trp Cys Gly Pro Cys Lys Met Ile Ala
                35                  40

Pro Ile Leu Asp Glu Ile Ala Asp Glu Tyr
                45                  50

Gln Gly Lys Leu Thr Val Ala Lys Leu Asn
                55                  60

Ile Asp Gln Asn Pro Gly Thr Ala Pro Lys
                65                  70

Tyr Gly Ile Arg Gly Ile Pro Thr Leu Leu
                75                  80

Leu Phe Lys Asn Gly Glu Val Ala Ala Thr
                85                  90

Lys Val Gly Ala Leu Ser Lys Gly Gln Leu
                95                 100

Lys Glu Phe Leu Asp Ala Asn Leu Ala Gly
               105                 110

Ser Gly Ser Gly His Met His His His His
               115                 120

His His Ser Ser Gly Leu Val Pro Arg Gly
               125                 130

Ser Gly Met Lys Glu Thr Ala Ala Ala Lys
               135                 140

Phe Glu Arg Gln His Met Asp Ser Pro Asp
               145                 150

Leu Gly Thr Asp Asp Asp Asp Lys Ala Met
               155                 160

Ala Asp Ile Gly Ser Ile Glu Gly Arg Gly
               165                 170

Thr Met Ala Ile Ser Val Thr Met Asp Asn
               175                 180

Ile Leu Ser Gly Phe Glu Asn Glu Tyr Asp
               185                 190

Val Ile Tyr Leu Lys Pro Leu Ala Gly Val
               195                 200

Tyr Arg Ser Leu Lys Lys Gln Ile Glu Lys
               205                 210
```

```
Asn Ile Phe Thr Phe Asn Leu Asn Leu Asn
            215                 220

Asp Ile Leu Asn Ser Arg Leu Lys Lys Arg
            225                 230

Lys Tyr Phe Leu Asp Val Leu Glu Ser Asp
            235                 240

Leu Met Gln Phe Lys His Ile Ser Ser Asn
            245                 250

Glu Tyr Ile Ile Glu Asp Ser Phe Lys Leu
            255                 260

Leu Asn Ser Glu Gln Lys Asn Thr Leu Leu
            265                 270

Lys Ser Tyr Lys Tyr Ile Lys Glu Ser Val
            275                 280

Glu Asn Asp Ile Lys Phe Ala Gln Glu Gly
            285                 290

Ile Ser Tyr Tyr Glu Lys Val Leu Ala Lys
            295                 300

Tyr Lys Asp Asp Leu Glu Ser Ile Lys Lys
            305                 310

Val Ile Lys Glu Glu Lys Glu Lys Phe Pro
            315                 320

Ser Ser Pro Pro Thr Thr Pro Pro Ser Pro
            325                 330

Ala Lys Thr Asp Glu Gln Lys Lys Glu Ser
            335                 340

Lys Phe Leu Pro Phe Leu Thr Asn Ile Glu
            345                 350

Thr Leu Tyr Asn Asn Leu Val Asn Lys Ile
            355                 360

Asp Asp Tyr Leu Ile Asn Leu Lys Ala Lys
            365                 370

Ile Asn Asp Cys Asn Val Glu Lys Asp Glu
            375                 380

Ala His Val Lys Ile Thr Lys Leu Ser Asp
            385                 390

Leu Lys Ala Ile Asp Asp Lys Ile Asp Leu
            395                 400

Phe Lys Asn Pro Tyr Asp Phe Glu Ala Ile
            405                 410

Lys Lys Leu Ile Asn Asp Asp Thr Lys Lys
            415                 420

Asp Met Leu Gly Lys Leu Leu Ser Thr Gly
            425                 430

Leu Val Gln Asn Phe Pro Asn Thr Ile Ile
            435                 440

Ser Lys Leu Ile Glu Gly Lys Phe Gln Asp
            445                 450

Met Leu Asn Ile Ser Gln His Gln Cys Val
            455                 460

Lys Lys Gln Cys Pro Glu Asn Ser Gly Cys
            465                 470
```

```
Phe Arg His Leu Asp Glu Arg Glu Glu Cys
                475                 480

Lys Cys Leu Leu Asn Tyr Lys Gln Glu Gly
                485                 490

Asp Lys Cys Val Glu Asn Pro Asn Pro Thr
                495                 500

Cys Asn Glu Asn Asn Gly Gly Cys Asp Ala
                505                 510

Asp Ala Thr Cys Thr Glu Glu Asp Ser Gly
                515                 520

Ser Ser Arg Lys Lys Ile Thr Cys Glu Cys
                525                 530

Thr Lys Pro Asp Ser Tyr Pro Leu Phe Asp
                535                 540

Gly Ile Phe Cys Ser Ser
                545

<210> SEQ ID NO 2
<211> LENGTH: 431
<212> TYPE: PRT
<213> ORGANISM: Artificial sequence
<220> FEATURE:
<223> OTHER INFORMATION: E. coli expressed P. falciparum MSP142 (3D7)
      Protein Sequence in pET(50)MSP1-42

<400> SEQUENCE: 2

Met His His His His His Ser Ser Gly
 1                5                 10

Leu Val Pro Arg Gly Ser Gly Met Lys Glu
                15                  20

Thr Ala Ala Ala Lys Phe Glu Arg Gln His
                25                  30

Met Asp Ser Pro Asp Leu Gly Thr Asp Asp
                35                  40

Asp Asp Lys Ala Met Ala Asp Ile Gly Ser
                45                  50

Ile Glu Gly Arg Gly Thr Met Ala Ile Ser
                55                  60

Val Thr Met Asp Asn Ile Leu Ser Gly Phe
                65                  70

Glu Asn Glu Tyr Asp Val Ile Tyr Leu Lys
                75                  80

Pro Leu Ala Gly Val Tyr Arg Ser Leu Lys
                85                  90

Lys Gln Ile Glu Lys Asn Ile Phe Thr Phe
                95                  100

Asn Leu Asn Leu Asn Asp Ile Leu Asn Ser
                105                 110

Arg Leu Lys Lys Arg Lys Tyr Phe Leu Asp
                115                 120

Val Leu Glu Ser Asp Leu Met Gln Phe Lys
                125                 130

His Ile Ser Ser Asn Glu Tyr Ile Ile Glu
                135                 140

Asp Ser Phe Lys Leu Leu Asn Ser Glu Gln
                145                 150
```

```
Lys Asn Thr Leu Leu Lys Ser Tyr Lys Tyr
                155                 160

Ile Lys Glu Ser Val Glu Asn Asp Ile Lys
                165                 170

Phe Ala Gln Glu Gly Ile Ser Tyr Tyr Glu
                175                 180

Lys Val Leu Ala Lys Tyr Lys Asp Asp Leu
                185                 190

Glu Ser Ile Lys Lys Val Ile Lys Glu Glu
                195                 200

Lys Glu Lys Phe Pro Ser Ser Pro Pro Thr
                205                 210

Thr Pro Pro Ser Pro Ala Lys Thr Asp Glu
                215                 220

Gln Lys Lys Glu Ser Lys Phe Leu Pro Phe
                225                 230

Leu Thr Asn Ile Glu Thr Leu Tyr Asn Asn
                235                 240

Leu Val Asn Lys Ile Asp Asp Tyr Leu Ile
                245                 250

Asn Leu Lys Ala Lys Ile Asn Asp Cys Asn
                255                 260

Val Glu Lys Asp Glu Ala His Val Lys Ile
                265                 270

Thr Lys Leu Ser Asp Leu Lys Ala Ile Asp
                275                 280

Asp Lys Ile Asp Leu Phe Lys Asn Pro Tyr
                285                 290

Asp Phe Glu Ala Ile Lys Lys Leu Ile Asn
                295                 300

Asp Asp Thr Lys Lys Asp Met Leu Gly Lys
                305                 310

Leu Leu Ser Thr Gly Leu Val Gln Asn Phe
                315                 320

Pro Asn Thr Ile Ile Ser Lys Leu Ile Glu
                325                 330

Gly Lys Phe Gln Asp Met Leu Asn Ile Ser
                335                 340

Gln His Gln Cys Val Lys Lys Gln Cys Pro
                345                 350

Glu Asn Ser Gly Cys Phe Arg His Leu Asp
                355                 360

Glu Arg Glu Glu Cys Lys Cys Leu Leu Asn
                365                 370

Tyr Lys Gln Glu Gly Asp Lys Cys Val Glu
                375                 380

Asn Pro Asn Pro Thr Cys Asn Glu Asn Asn
                385                 390

Gly Gly Cys Asp Ala Asp Ala Thr Cys Thr
                395                 400

Glu Glu Asp Ser Gly Ser Ser Arg Lys Lys
                405                 410
```

```
Ile Thr Cys Glu Cys Thr Lys Pro Asp Ser
                415                 420

Tyr Pro Leu Phe Asp Gly Ile Phe Cys Ser
                425                 430

Ser

<210> SEQ ID NO 3
<211> LENGTH: 393
<212> TYPE: PRT
<213> ORGANISM: Artificial sequence
<220> FEATURE:
<223> OTHER INFORMATION: E. coli expressed P. falciparum MSP142 (3D7)
      Protein Sequence in pET42A

<400> SEQUENCE: 3

Met Ala His His His His His His Pro Gly
  1               5                  10

Gly Ser Ile Glu Gly Arg Gly Thr Met Ala
                 15                  20

Ile Ser Val Thr Met Asp Asn Ile Leu Ser
                 25                  30

Gly Phe Glu Asn Glu Tyr Asp Val Ile Tyr
                 35                  40

Leu Lys Pro Leu Ala Gly Val Tyr Arg Ser
                 45                  50

Leu Lys Lys Gln Ile Glu Lys Asn Ile Phe
                 55                  60

Thr Phe Asn Leu Asn Leu Asn Asp Ile Leu
                 65                  70

Asn Ser Arg Leu Lys Lys Arg Lys Tyr Phe
                 75                  80

Leu Asp Val Leu Glu Ser Asp Leu Met Gln
                 85                  90

Phe Lys His Ile Ser Ser Asn Glu Tyr Ile
                 95                 100

Ile Glu Asp Ser Phe Lys Leu Leu Asn Ser
                105                 110

Glu Gln Lys Asn Thr Leu Leu Lys Ser Tyr
                115                 120

Lys Tyr Ile Lys Glu Ser Val Glu Asn Asp
                125                 130

Ile Lys Phe Ala Gln Glu Gly Ile Ser Tyr
                135                 140

Tyr Glu Lys Val Leu Ala Lys Tyr Lys Asp
                145                 150

Asp Leu Glu Ser Ile Lys Lys Val Ile Lys
                155                 160

Glu Glu Lys Glu Lys Phe Pro Ser Ser Pro
                165                 170

Pro Thr Thr Pro Pro Ser Pro Ala Lys Thr
                175                 180

Asp Glu Gln Lys Lys Glu Ser Lys Phe Leu
                185                 190

Pro Phe Leu Thr Asn Ile Glu Thr Leu Tyr
                195                 200
```

```
Asn Asn Leu Val Asn Lys Ile Asp Asp Tyr
            205                 210
Leu Ile Asn Leu Lys Ala Lys Ile Asn Asp
            215                 220
Cys Asn Val Glu Lys Asp Glu Ala His Val
            225                 230
Lys Ile Thr Lys Leu Ser Asp Leu Lys Ala
            235                 240
Ile Asp Asp Lys Ile Asp Leu Phe Lys Asn
            245                 250
Pro Tyr Asp Phe Glu Ala Ile Lys Lys Leu
            255                 260
Ile Asn Asp Asp Thr Lys Lys Asp Met Leu
            265                 270
Gly Lys Leu Leu Ser Thr Gly Leu Val Gln
            275                 280
Asn Phe Pro Asn Thr Ile Ile Ser Lys Leu
            285                 290
Ile Glu Gly Lys Phe Gln Asp Met Leu Asn
            295                 300
Ile Ser Gln His Gln Cys Val Lys Lys Gln
            305                 310
Cys Pro Glu Asn Ser Gly Cys Phe Arg His
            315                 320
Leu Asp Glu Arg Glu Glu Cys Lys Cys Leu
            325                 330
Leu Asn Tyr Lys Gln Glu Gly Asp Lys Cys
            335                 340
Val Glu Asn Pro Asn Pro Thr Cys Asn Glu
            345                 350
Asn Asn Gly Gly Cys Asp Ala Asp Ala Thr
            355                 360
Cys Thr Glu Glu Asp Ser Gly Ser Ser Arg
            365                 370
Lys Lys Ile Thr Cys Glu Cys Thr Lys Pro
            375                 380
Asp Ser Tyr Pro Leu Phe Asp Gly Ile Phe
            385                 390
Cys Ser Ser

<210> SEQ ID NO 4
<211> LENGTH: 1140
<212> TYPE: DNA
<213> ORGANISM: Plasmodium falciparum 3D7 MSP142

<400> SEQUENCE: 4
ggtaccatgg caatatctgt cacaatggat aatatcctct            40
caggatttga aaatgaatat gatgttatat atttaaaacc            80
tttagctgga gtatatagaa gcttaaaaaa acaaattgaa           120
aaaaacattt ttacatttaa tttaaatttg aacgatatct           160
taaattcacg tcttaagaaa cgaaaatatt tcttagatgt           200
attagaatct gatttaatgc aatttaaaca tatatcctca           240
```

```
aatgaataca ttattgaaga ttcatttaaa ttattgaatt                    280
cagaacaaaa aaacacactt ttaaaaagtt acaaatatat                    320
aaaagaatca gtagaaaatg atattaaatt tgcacaggaa                    360
ggtataagtt attatgaaaa ggttttagcg aaatataagg                    400
atgatttaga atcaattaaa aaagttatca aagaagaaaa                    440
ggagaagttc ccatcatcac caccaacaac acctccgtca                    480
ccagcaaaaa cagacgaaca aaagaaggaa agtaagttcc                    520
ttccattttt aacaaacatt gagacctttat acaataactt                   560 agttaataaa attgacgatt acttaattaa cttaaaggca                    600
aagattaacg attgtaatgt tgaaaaagat gaagcacatg                    640
ttaaaataac taaacttagt gatttaaaag caattgatga                    680
caaaatagat ctttttaaaa accctaccga cttcgaagca                    720
attaaaaaat tgataaatga tgatacgaaa aaagatatgc                    760
ttggcaaatt acttagtaca ggattagttc aaattttcc                     800 taatacaata atatcaaaat taattgaagg aaaattccaa                    840
gatatgttaa acatttcaca acaccaatgc gtaaaaaaac                    880
aatgtccaga aaattctgga tgtttcagac atttagatga                    920
aagagaagaa tgtaaatgtt tattaaatta caaacaagaa                    960
ggtgataaat gtgttgaaaa tccaaatcct acttgtaacg                    1000
aaaataatgg tggatgtgat gcagatgcca catgtaccga                    1040
agaagattca ggtagcagca gaaagaaaat cacatgtgaa                    1080
tgtactaaac ctgattctta tccactttc gatggtattt                     1120 tctgcagttc ctaagtcgac                                          1140
```

<210> SEQ ID NO 5
<211> LENGTH: 383
<212> TYPE: PRT
<213> ORGANISM: Plasmodium falciparum 3D7 MSP142

<400> SEQUENCE: 5

```
Gly Ser Ile Glu Gly Arg Gly Thr Met Ala
 1               5                  10

Ile Ser Val Thr Met Asp Asn Ile Leu Ser
            15                  20

Gly Phe Glu Asn Glu Tyr Asp Val Ile Tyr
            25                  30

Leu Lys Pro Leu Ala Gly Val Tyr Arg Ser
            35                  40

Leu Lys Lys Gln Ile Glu Lys Asn Ile Phe
            45                  50

Thr Phe Asn Leu Asn Leu Asn Asp Ile Leu
            55                  60

Asn Ser Arg Leu Lys Lys Arg Lys Tyr Phe
            65                  70

Leu Asp Val Leu Glu Ser Asp Leu Met Gln
            75                  80
```

```
Phe Lys His Ile Ser Ser Asn Glu Tyr Ile
                85                  90

Ile Glu Asp Ser Phe Lys Leu Leu Asn Ser
                95                 100

Glu Gln Lys Asn Thr Leu Leu Lys Ser Tyr
               105                 110

Lys Tyr Ile Lys Glu Ser Val Glu Asn Asp
               115                 120

Ile Lys Phe Ala Gln Glu Gly Ile Ser Tyr
               125                 130

Tyr Glu Lys Val Leu Ala Lys Tyr Lys Asp
               135                 140

Asp Leu Glu Ser Ile Lys Lys Val Ile Lys
               145                 150

Glu Glu Lys Glu Lys Phe Pro Ser Ser Pro
               155                 160

Pro Thr Thr Pro Pro Ser Pro Ala Lys Thr
               165                 170

Asp Glu Gln Lys Lys Glu Ser Lys Phe Leu
               175                 180

Pro Phe Leu Thr Asn Ile Glu Thr Leu Tyr
               185                 190

Asn Asn Leu Val Asn Lys Ile Asp Asp Tyr
               195                 200

Leu Ile Asn Leu Lys Ala Lys Ile Asn Asp
               205                 210

Cys Asn Val Glu Lys Asp Glu Ala His Val
               215                 220

Lys Ile Thr Lys Leu Ser Asp Leu Lys Ala
               225                 230

Ile Asp Asp Lys Ile Asp Leu Phe Lys Asn
               235                 240

Pro Thr Asp Phe Glu Ala Ile Lys Lys Leu
               245                 250

Ile Asn Asp Asp Thr Lys Lys Asp Met Leu
               255                 260

Gly Lys Leu Leu Ser Thr Gly Leu Val Gln
               265                 270

Ile Phe Pro Asn Thr Ile Ile Ser Lys Leu
               275                 280

Ile Glu Gly Lys Phe Gln Asp Met Leu Asn
               285                 290

Ile Ser Gln His Gln Cys Val Lys Lys Gln
               295                 300

Cys Pro Glu Asn Ser Gly Cys Phe Arg His
               305                 310

Leu Asp Glu Arg Glu Cys Lys Cys Leu
               315                 320

Leu Asn Tyr Lys Gln Glu Gly Asp Lys Cys
               325                 330

Val Glu Asn Pro Asn Pro Thr Cys Asn Glu
               335                 340
```

```
Asn Asn Gly Gly Cys Asp Ala Asp Ala Thr
            345                 350

Cys Thr Glu Glu Asp Ser Gly Ser Ser Arg
            355                 360

Lys Lys Ile Thr Cys Glu Cys Thr Lys Pro
            365                 370

Asp Ser Tyr Pro Leu Phe Asp Gly Ile Phe
            375                 380

Cys Ser Ser

<210> SEQ ID NO 6
<211> LENGTH: 1176
<212> TYPE: DNA
<213> ORGANISM: Artificial sequence
<220> FEATURE:
<223> OTHER INFORMATION: E. coli expressed P. falciparum MSP-142 (3D7)

<400> SEQUENCE: 6
atggcacacc atcatcatca tcatcccggg ggatccggtt                    40
ctggtaccat ggcaatatct gtcacaatgg ataatatcct                    80
ctcaggattt gaaaatgaat atgatgttat atatttaaaa                   120
cctttagctg gagtatatag aagcttaaaa aaacaaattg                   160
aaaaaaacat ttttacattt aatttaaatt tgaacgatat                   200
cttaaattca cgtcttaaga acgaaaata tttcttagat                    240 gtattagaat ctgatttaat gcaatttaaa catatatcct                   280
caaatgaata cattattgaa gattcattta attattgaa                    320 ttcagaacaa aaaacacac ttttaaaaag ttacaaatat                    360
ataaaagaat cagtagaaaa tgatattaaa tttgcacagg                   400
aaggtataag ttattatgaa aaggttttag cgaaatataa                   440
ggatgattta gaatcaatta aaaaagttat caaagaagaa                   480
aaggagaagt tcccatcatc accaccaaca cacctccgt                    520 caccagcaaa aacagacgaa caaaagaagg aaagtaagtt                   560
ccttccattt ttaacaaaca ttgagacctt atacaataac                   600
ttagttaata aaattgacga ttacttaatt aacttaaagg                   640
caaagattaa cgattgtaat gttgaaaaag atgaagcaca                   680
tgttaaaata actaaactta gtgatttaaa agcaattgat                   720
gacaaaatag atcttttaa aaaccttac gacttcgaag                     760 caattaaaaa attgataaat gatgatacga aaaagatat                    800 gcttggcaaa ttacttagta caggattagt tcaaatttt                    840 cctaatacaa taatatcaaa attaattgaa ggaaaattcc                   880
aagatatgtt aaacatttca caacaccaat gcgtaaaaaa                   920
acaatgtcca gaaaattctg atgtttcag acatttagat                    960 gaaagagaag aatgtaaatg tttattaaat tacaaacaag                  1000
aaggtgataa atgtgttgaa atccaaatc ctacttgtaa                   1040 cgaaaatat ggtggatgtg atgcagatgc cacatgtacc                   1080
gaagaagatt caggtagcag cagaaagaaa atcacatgtg                  1120
```

```
aatgtactaa acctgattct tatccacttt tcgatggtat                    1160
tttctgcagt tcctaa                                              1176
```

<210> SEQ ID NO 7
<211> LENGTH: 391
<212> TYPE: PRT
<213> ORGANISM: Artificial sequence
<220> FEATURE:
<223> OTHER INFORMATION: E. coli expressed P. falciparum MSP-142 (3D7)

<400> SEQUENCE: 7

```
Met Ala His His His His His Pro Gly
 1               5                  10

Gly Ser Gly Ser Gly Thr Met Ala Ile Ser
                15                  20

Val Thr Met Asp Asn Ile Leu Ser Gly Phe
                    25                  30

Glu Asn Glu Tyr Asp Val Ile Tyr Leu Lys
                        35                  40

Pro Leu Ala Gly Val Tyr Arg Ser Leu Lys
                        45                  50

Lys Gln Ile Glu Lys Asn Ile Phe Thr Phe
                        55                  60

Asn Leu Asn Leu Asn Asp Ile Leu Asn Ser
                        65                  70

Arg Leu Lys Lys Arg Lys Tyr Phe Leu Asp
                        75                  80

Val Leu Glu Ser Asp Leu Met Gln Phe Lys
                        85                  90

His Ile Ser Ser Asn Glu Tyr Ile Ile Glu
                        95                  100

Asp Ser Phe Lys Leu Leu Asn Ser Glu Gln
                        105                 110

Lys Asn Thr Leu Leu Lys Ser Tyr Lys Tyr
                        115                 120

Ile Lys Glu Ser Val Glu Asn Asp Ile Lys
                        125                 130

Phe Ala Gln Glu Gly Ile Ser Tyr Tyr Glu
                        135                 140

Lys Val Leu Ala Lys Tyr Lys Asp Asp Leu
                        145                 150

Glu Ser Ile Lys Lys Val Ile Lys Glu Glu
                        155                 160

Lys Glu Lys Phe Pro Ser Ser Pro Pro Thr
                        165                 170

Thr Pro Pro Ser Pro Ala Lys Thr Asp Glu
                        175                 180

Gln Lys Lys Glu Ser Lys Phe Leu Pro Phe
                        185                 190

Leu Thr Asn Ile Glu Thr Leu Tyr Asn Asn
                        195                 200

Leu Val Asn Lys Ile Asp Asp Tyr Leu Ile
                        205                 210

Asn Leu Lys Ala Lys Ile Asn Asp Cys Asn
                        215                 220
```

-continued

```
Val Glu Lys Asp Glu Ala His Val Lys Ile
            225                 230

Thr Lys Leu Ser Asp Leu Lys Ala Ile Asp
            235                 240

Asp Lys Ile Asp Leu Phe Lys Asn Pro Tyr
            245                 250

Asp Phe Glu Ala Ile Lys Lys Leu Ile Asn
            255                 260

Asp Asp Thr Lys Lys Asp Met Leu Gly Lys
            265                 270

Leu Leu Ser Thr Gly Leu Val Gln Asn Phe
            275                 280

Pro Asn Thr Ile Ile Ser Lys Leu Ile Glu
            285                 290

Gly Lys Phe Gln Asp Met Leu Asn Ile Ser
            295                 300

Gln His Gln Cys Val Lys Lys Gln Cys Pro
            305                 310

Glu Asn Ser Gly Cys Phe Arg His Leu Asp
            315                 320

Glu Arg Glu Glu Cys Lys Cys Leu Leu Asn
            325                 330

Tyr Lys Gln Glu Gly Asp Lys Cys Val Glu
            335                 340

Asn Pro Asn Pro Thr Cys Asn Glu Asn Asn
            345                 350

Gly Gly Cys Asp Ala Asp Ala Thr Cys Thr
            355                 360

Glu Glu Asp Ser Gly Ser Ser Arg Lys Lys
            365                 370

Ile Thr Cys Glu Cys Thr Lys Pro Asp Ser
            375                 380

Tyr Pro Leu Phe Asp Gly Ile Phe Cys Ser
            385                 390

Ser

<210> SEQ ID NO 8
<211> LENGTH: 24
<212> TYPE: DNA
<213> ORGANISM: Artificial sequence
<220> FEATURE:
<223> OTHER INFORMATION: CpG oligonucleotide

<400> SEQUENCE: 8
tcgtcgtttt gtcgttttgt cgtt                                          24

<210> SEQ ID NO 9
<211> LENGTH: 48
<212> TYPE: DNA
<213> ORGANISM: Artificial sequence
<220> FEATURE:
<223> OTHER INFORMATION: PCR primer

<400> SEQUENCE: 9
ggggatccat tgagggtcgt ggtaccatgg caatatctgt                          40
cacaatgg                                                            48
```

```
<210> SEQ ID NO 10
<211> LENGTH: 29
<212> TYPE: DNA
<213> ORGANISM: Artificial sequence
<220> FEATURE:
<223> OTHER INFORMATION: PCR primer

<400> SEQUENCE: 10
gtcgacttag gaactgcaga aaataccgg                                    29

<210> SEQ ID NO 11
<211> LENGTH: 45
<212> TYPE: DNA
<213> ORGANISM: Artificial sequence
<220> FEATURE:
<223> OTHER INFORMATION: PCR primer

<400> SEQUENCE: 11
gggcatatgg cacaccatca tcatcatcat cccgggggat                        40
ccgac                                                              45

<210> SEQ ID NO 12
<211> LENGTH: 57
<212> TYPE: DNA
<213> ORGANISM: Artificial sequence
<220> FEATURE:
<223> OTHER INFORMATION: PCR primer

<400> SEQUENCE: 12
gggcatatgg cacaccatca tcatcatcat cccgggggat                        40
ccggttctgg taccgac                                                 57
```